US010295467B2

(12) United States Patent
Han et al.

(10) Patent No.: US 10,295,467 B2
(45) Date of Patent: May 21, 2019

(54) COMPOSITIONS AND METHODS FOR UPCONVERTING LUMINESCENCE WITH ENGINEERED EXCITATION AND APPLICATIONS THEREOF

(71) Applicant: University of Massachusetts Medical School, Boston, MA (US)

(72) Inventors: Gang Han, Shrewsbury, MA (US); Jie Shen, Worcester, MA (US)

(73) Assignee: University of Massachusetts, Boston, MA (US)

( * ) Notice: Subject to any disclaimer, the term of this patent is extended or adjusted under 35 U.S.C. 154(b) by 665 days.

(21) Appl. No.: 14/761,546

(22) PCT Filed: Jan. 22, 2014

(86) PCT No.: PCT/US2014/012437
§ 371 (c)(1),
(2) Date: Jul. 16, 2015

(87) PCT Pub. No.: WO2014/116631
PCT Pub. Date: Jul. 31, 2014

(65) Prior Publication Data
US 2015/0362432 A1 Dec. 17, 2015

Related U.S. Application Data

(60) Provisional application No. 61/755,424, filed on Jan. 22, 2013.

(51) Int. Cl.
*A61K 9/00* (2006.01)
*G01N 21/64* (2006.01)
(Continued)

(52) U.S. Cl.
CPC .......... *G01N 21/6428* (2013.01); *C09K 11/02* (2013.01); *C09K 11/025* (2013.01);
(Continued)

(58) Field of Classification Search
CPC .................................. G01N 21/6428
See application file for complete search history.

(56) References Cited

U.S. PATENT DOCUMENTS 7,651,771 B2 * 1/2010 Meyer ................ C09K 11/7741
428/403
2012/0064134 A1 * 3/2012 Bourke, Jr. ............ A61Q 17/04
424/401

OTHER PUBLICATIONS

Wang et al. "Simultaneous phase and size control of upconversion nanocrystals through lanthanide doping", Nature, vol. 463, Feb. 25, 2010.*

(Continued)

*Primary Examiner* — Paul W Dickinson
(74) *Attorney, Agent, or Firm* — Milstein Zhang & Wu LLC

(57) ABSTRACT

The invention generally relates to materials and methods for creating and/or utilizing upconverting luminescence. More particularly, the invention relates to novel compositions (e.g., nanoparticles) and related methods of preparation and use that enable upconverting luminescence with an efficient excitation optimized at about 800 nm. A unique class of cascade sensitized tri-doped UCNPs with a biocompatible 800 nm excitable property are disclosed herein, for example, tri-doped β-NaYF$_4$:Nd,Yb,Er(Tm)/NaYF$_4$ UCNPs, which employ Nd$^{3+}$ as 800 nm photon sensitizer and Yb$^{3+}$ as bridging ions, having strong green or blue upconversion emissions without photobleaching.

6 Claims, 23 Drawing Sheets

Spectra profiles of tissue optical window. The extinction coefficient of water at 800 nm is about 20 timers lower than that at 980 nm.

(51) Int. Cl.
 *C09K 11/02* (2006.01)
 *C09K 11/77* (2006.01)
(52) U.S. Cl.
 CPC ...... *C09K 11/7773* (2013.01); *G01N 21/6486* (2013.01); *G01N 2021/6439* (2013.01); *G01N 2458/30* (2013.01); *G01N 2458/40* (2013.01); *Y10T 436/143333* (2015.01)

(56) References Cited

OTHER PUBLICATIONS

Wang et al, Simultaneous phase and size control of upconversion nanocrystals through lanthanide doping, Nature, 2010, 463,1061-1065 (Year: 2010).*

* cited by examiner

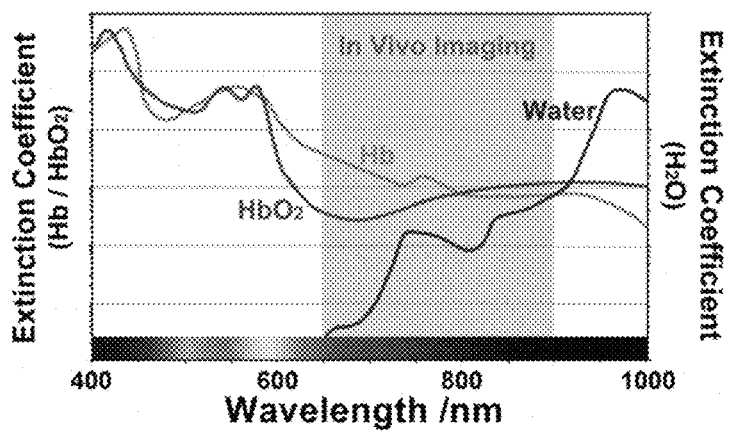
FIG. 1. Spectra profiles of tissue optical window. The extinction coefficient of water at 800 nm is about 20 timers lower than that at 980 nm.

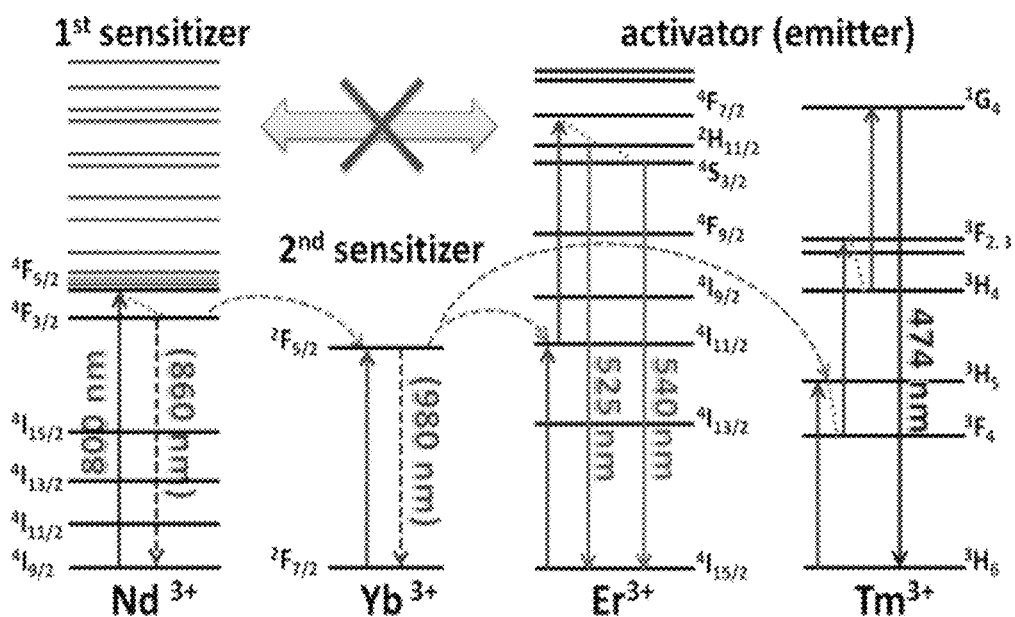
FIG. 2. Upconversion process of $Nd^{3+} \rightarrow Yb^{3+} \rightarrow Er^{3+}(Tm^{3+})$ tri-dopants system with 800 nm excitation.

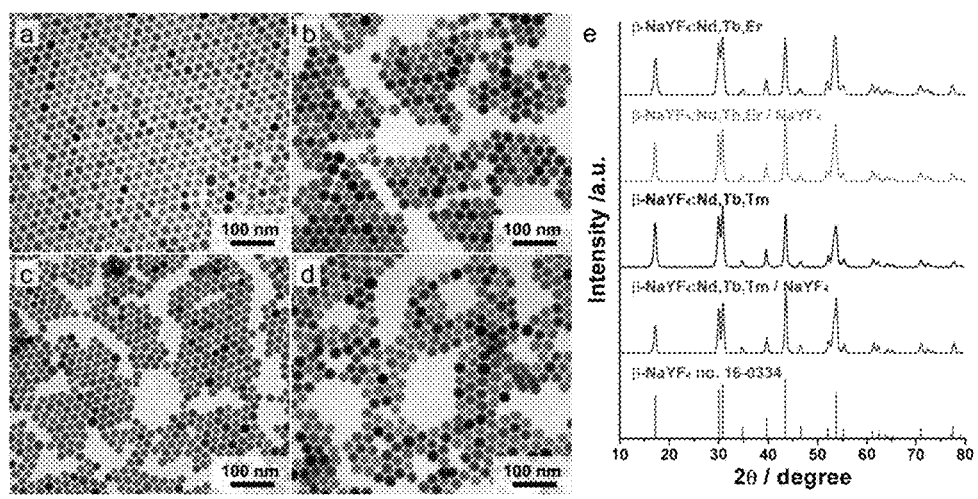
FIG. 3. Transmission Electron Microscopy (TEM) images of (a) β-NaYF$_4$:0.5%Nd,20%Yb,2%Er, (b) β-NaYF$_4$:Nd,Yb,Er/NaYF$_4$, (c) β-NaYF$_4$:1%Nd,30%Yb,0.5%Tm and (d) β-NaYF$_4$:Nd,Yb,Tm/NaYF$_4$ UCNPs. (e) The X-ray Diffraction (XRD) patterns of four samples and index data of β-NaYF$_4$.

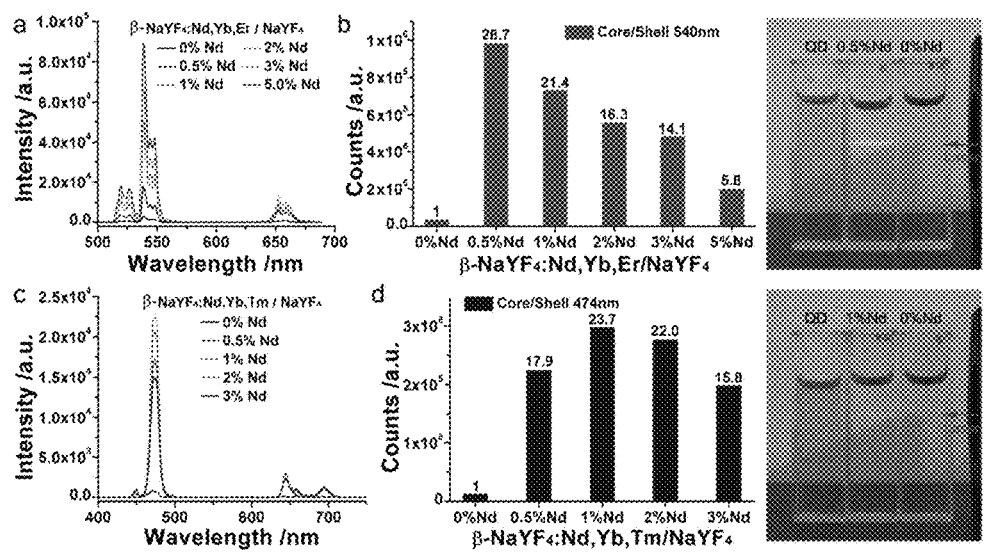
FIG. 4. The upconverting emission spectra and emission counts summary of (a, b) β-NaYF$_4$:(0-5%)Nd,20%Yb,2%Er /NaYF$_4$ and (c, d) β-NaYF$_4$:(0-3%)Nd,30%Yb,0.5%Tm /NaYF$_4$ UCNPs. The measurement was applied under 800 nm CW laser excitation (6.0 W/cm$^2$) using the concentration normalized UCNPs solutions. The upconverting luminescent pictures were inserted in (b, d) with the laser path labeled.

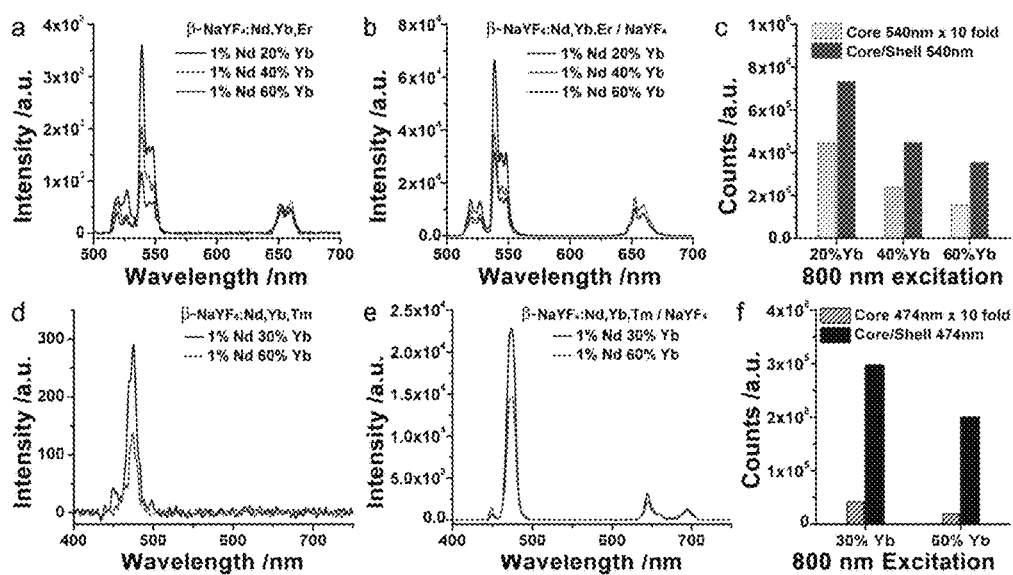
FIG. 5. The upconverting emission spectra and emission counts of (a, b, c) β-NaYF$_4$:Nd,Yb,Er core and core/shell UCNPs, (d, e, f) β-NaYF$_4$:Nd,Yb,Tm core and core/shell UCNPs under 800 nm CW laser excitation (6.0 W/cm$^2$). All of the UCNPs solutions have the same particle concentrations.

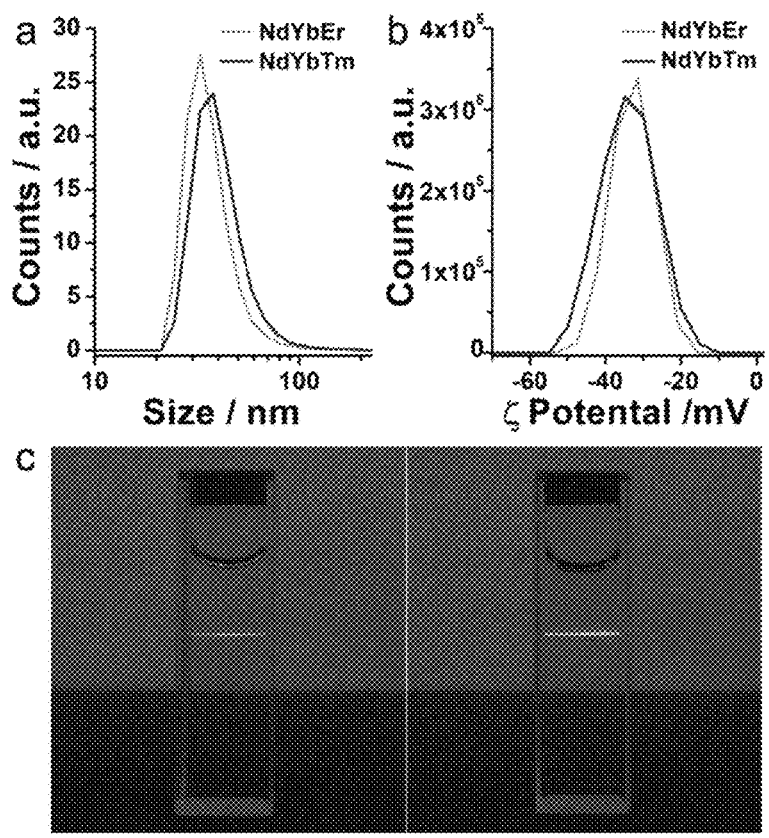
FIG. 6. (a) Hydrodynamics size, (b) ζ potential distributions of PAA modified β-NaYF$_4$:0.5%Nd, 20%Yb, 2%Er /NaYF$_4$ and β-NaYF$_4$:1%Nd, 30%Yb, 0.5%Tm /NaYF$_4$ UCNPs, and (c) 800 nm excited upconverting luminescence.

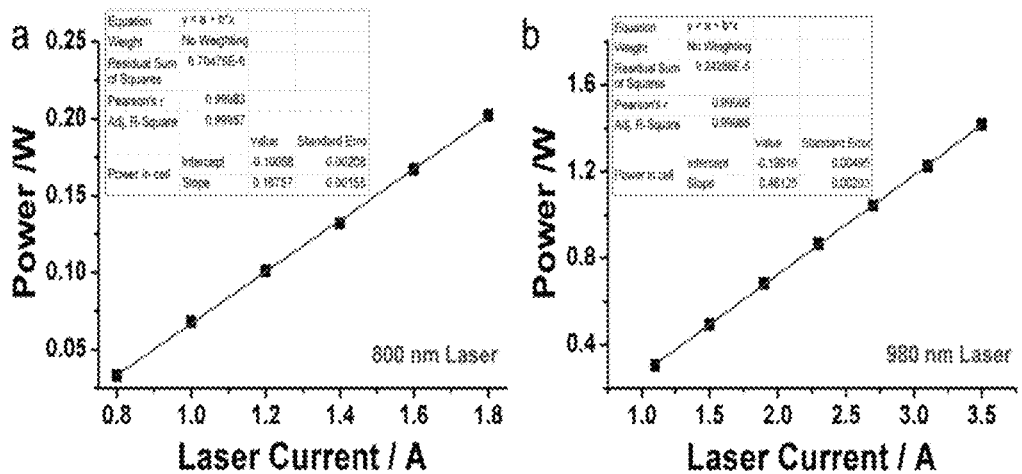
FIG. 7. The output power of (a) the 800 nm CW laser and (b) the 980 nm laser under different operating laser currents.
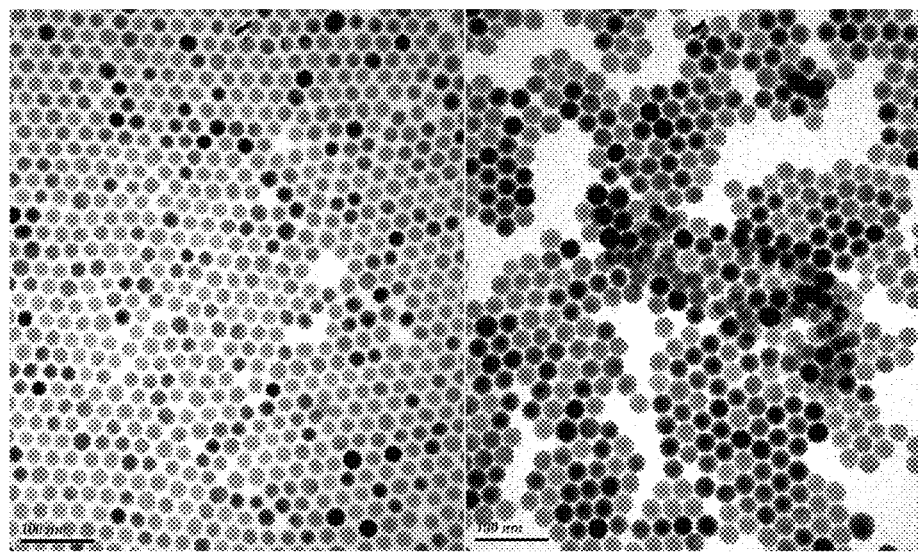
FIG. 8. β-NaYF$_4$:0.5%Nd,20%Yb,2%Er (left) and the corresponding core/shell (right) UCNPs. Their respective statistical sizes are 20.2±1.6 nm and 29.5±1.0 nm.

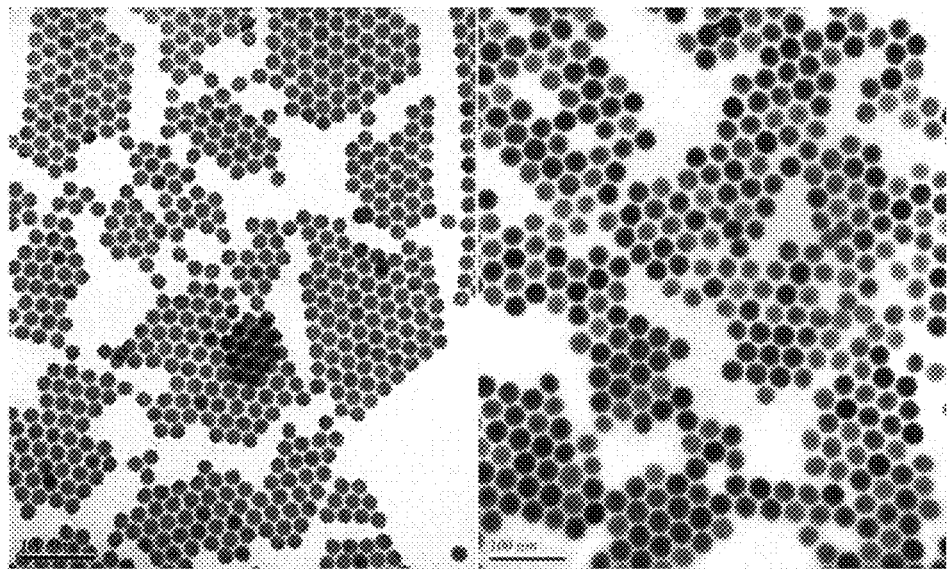
FIG. 9. β-NaYF$_4$:1%Nd,20%Yb,2%Er (left) and the corresponding core/shell (right) UCNPs. Their respective statistical sizes are 20.4±0.6 nm and 29.2±0.9 nm.
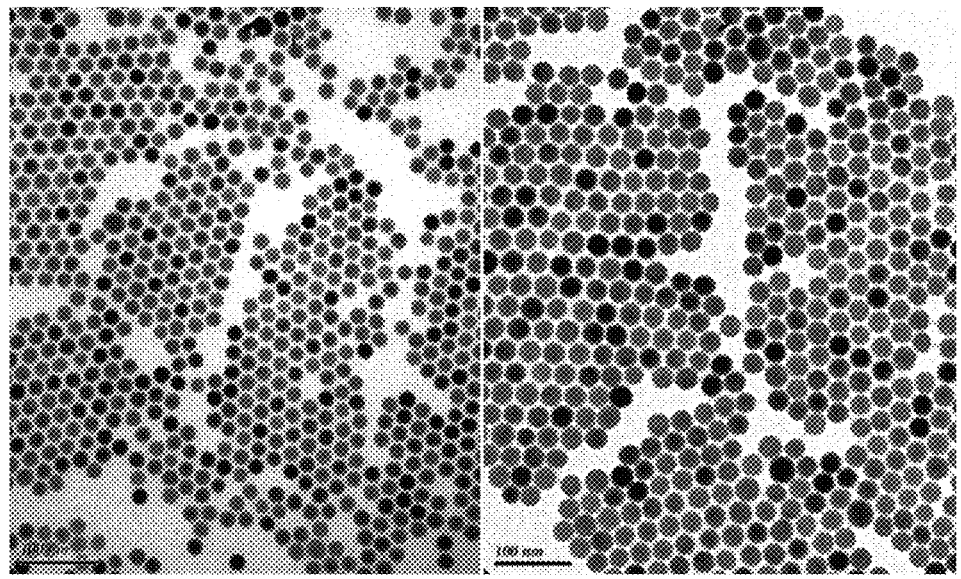
FIG. 10. β-NaYF$_4$:2%Nd,20%Yb,2%Er (left) and the corresponding core/shell (right) UCNPs. Their statistical sizes are 20.3±1.2 nm and 29.0±1.3 nm.

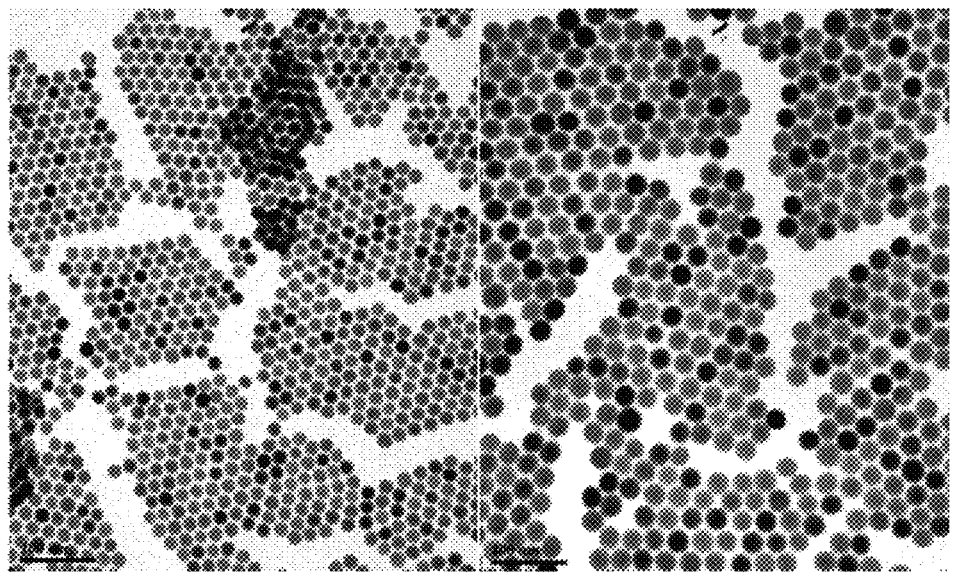
FIG. 11. β-NaYF$_4$:3%Nd,20%Yb,2%Er (left) and the corresponding core/shell (right) UCNPs. Their respective statistical sizes are 19.7±0.7 nm and 29.3±1.2 nm.
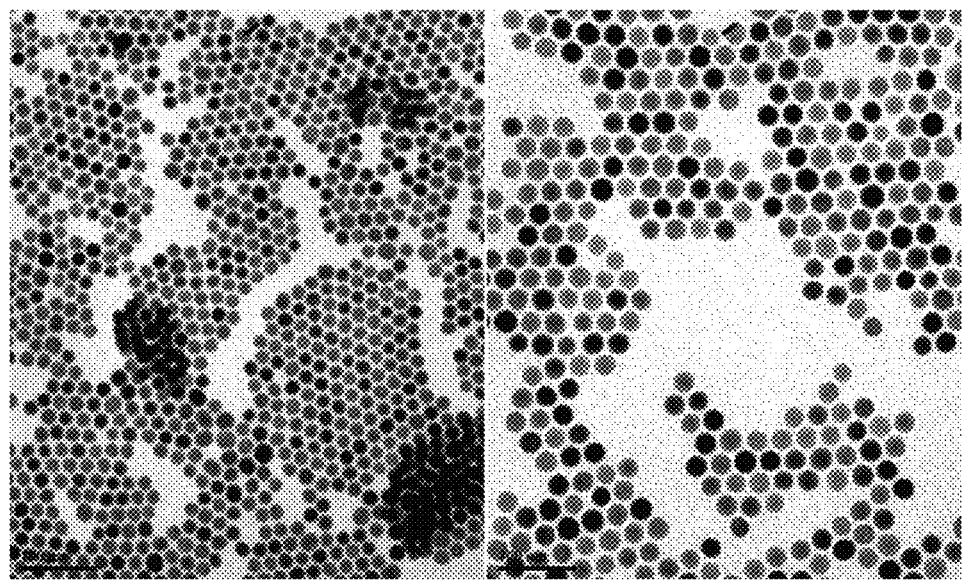
FIG. 12. β-NaYF$_4$:5%Nd,20%Yb,2%Er (left) and the corresponding core/shell (right) UCNPs. Their respective statistical sizes are 19.9±1.4 nm and 28.8±0.9 nm.

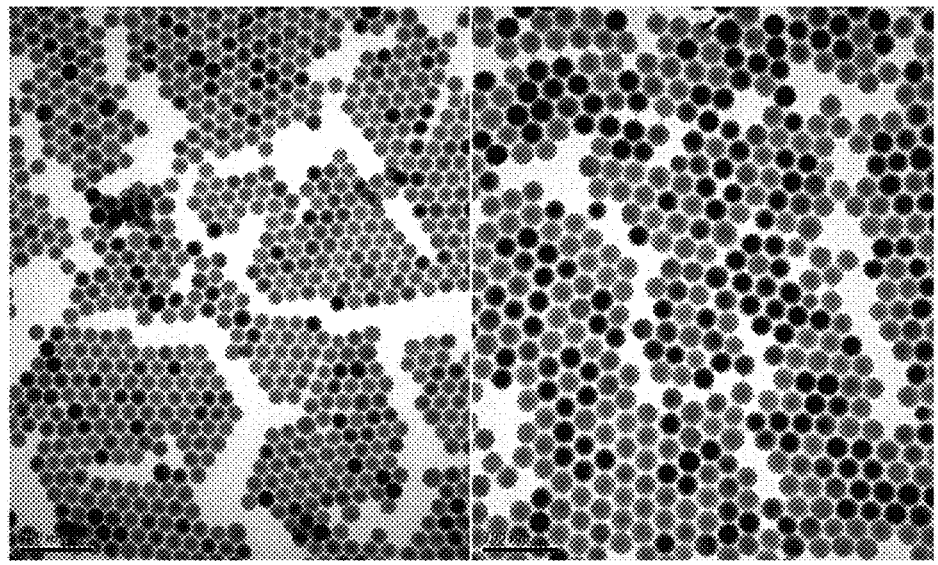
FIG. 13. β-NaYF$_4$:1%Nd,40%Yb,2%Er (left) and the corresponding core/shell (right) UCNPs. Their respective statistical sizes are 21.2±1.0 nm and 29.4±1.4 nm.
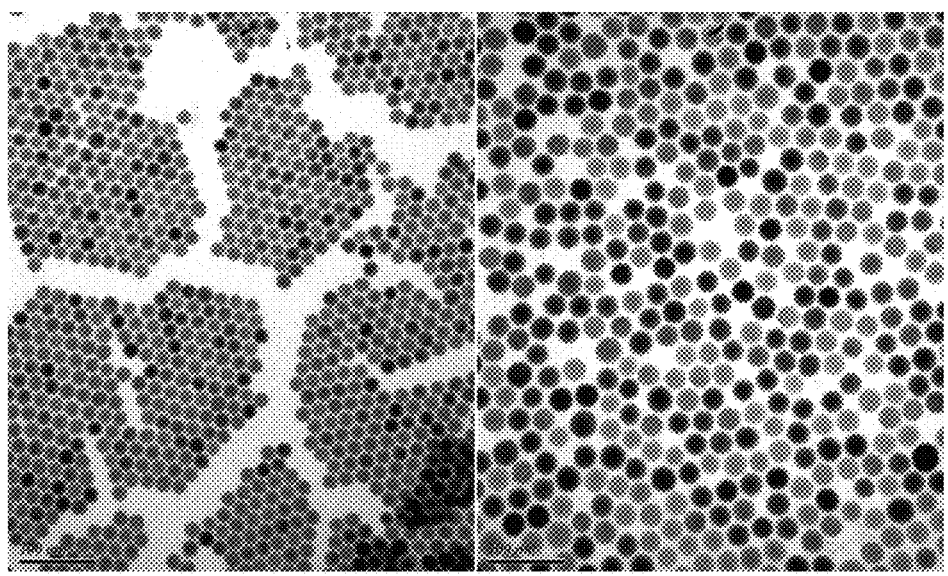
FIG. 14. β-NaYF$_4$:1%Nd,60%Yb,2%Er (left) and the corresponding core/shell (right) UCNPs. Their respective statistical sizes are 20.5±0.8 nm and 29.1±2.3 nm.

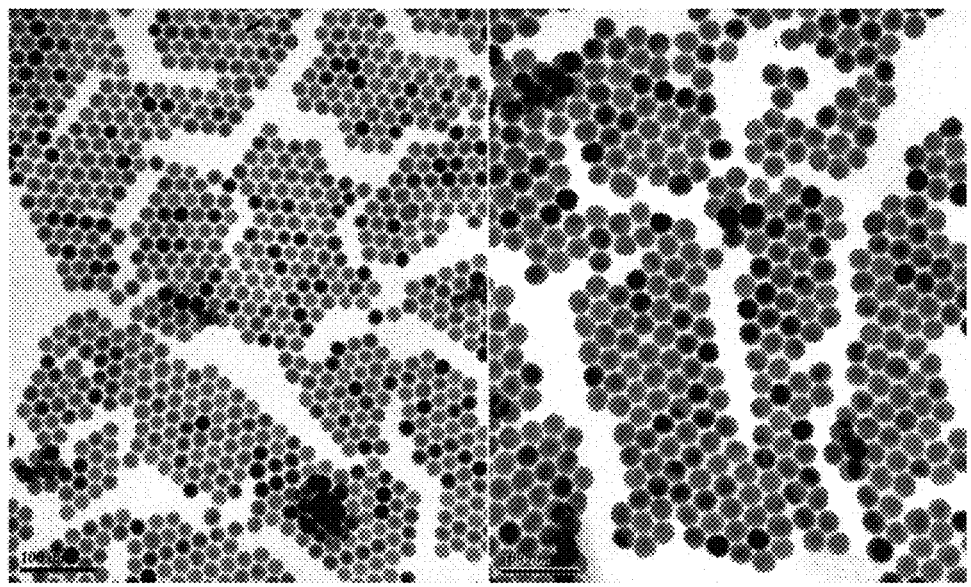
FIG. 15. β-NaYF$_4$:20%Yb,2%Er (left) and the corresponding core/shell (right) UCNPs. Their respective statistical sizes are 20.7±0.7 nm and 29.8±0.5 nm.
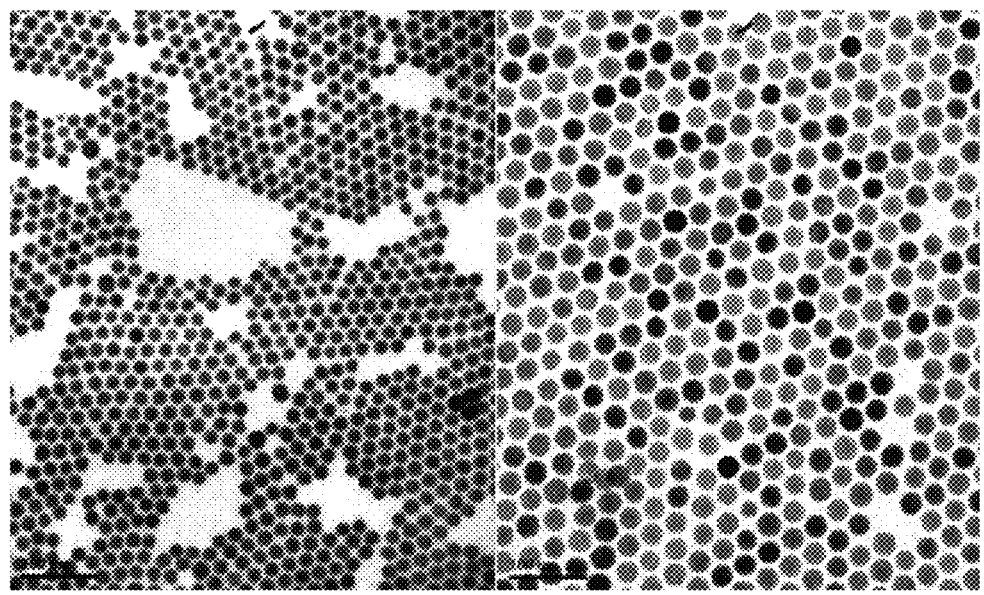
FIG. 16. β-NaYF$_4$:0.5%Nd,30%Yb,0.5%Tm (left) and the corresponding core/shell (right) UCNPs. Their respective statistical sizes are 20.0±1.1 nm and 29.1±0.5 nm.

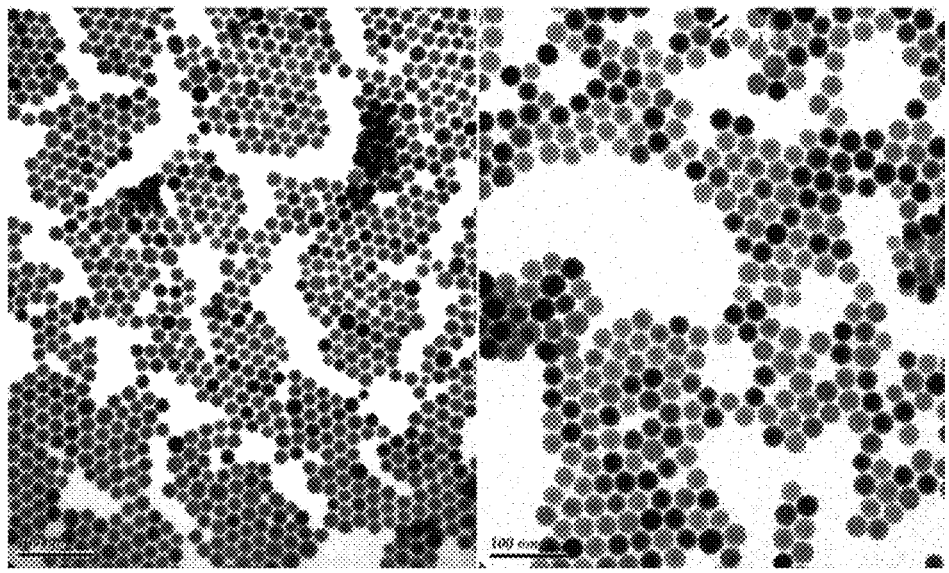
FIG. 17. β-NaYF$_4$:1%Nd,30%Yb,0.5%Tm (left) and the corresponding core/shell (right) UCNPs. Their respective statistical sizes are 20.5±1.9 nm and 29.1±1.2 nm.
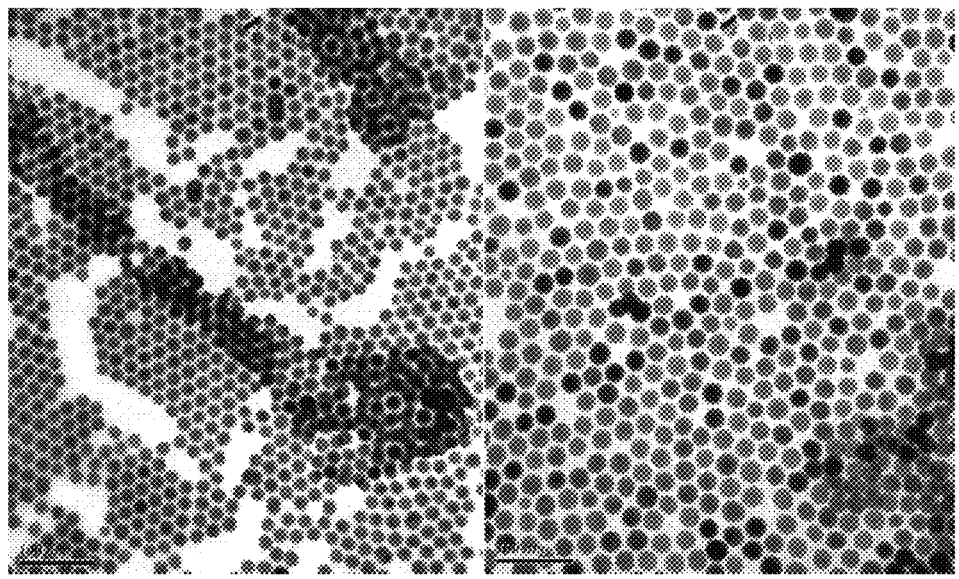
FIG. 18. β-NaYF$_4$:2%Nd,30%Yb,0.5%Tm (left) and the corresponding core/shell (right) UCNPs. Their respective statistical sizes are 20.1±1.7 nm and 29.3±1.8 nm.

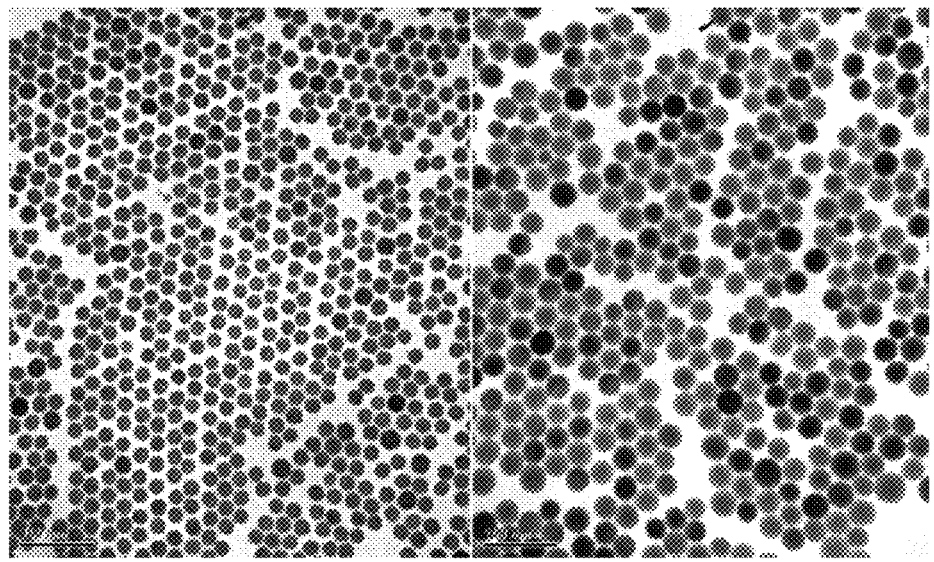
FIG. 19. β-NaYF$_4$:1%Nd,60%Yb,0.5%Tm (left) and the corresponding core/shell (right) UCNPs. Their respective statistical sizes are 20.4±1.3 nm and 29.8±1.9 nm.
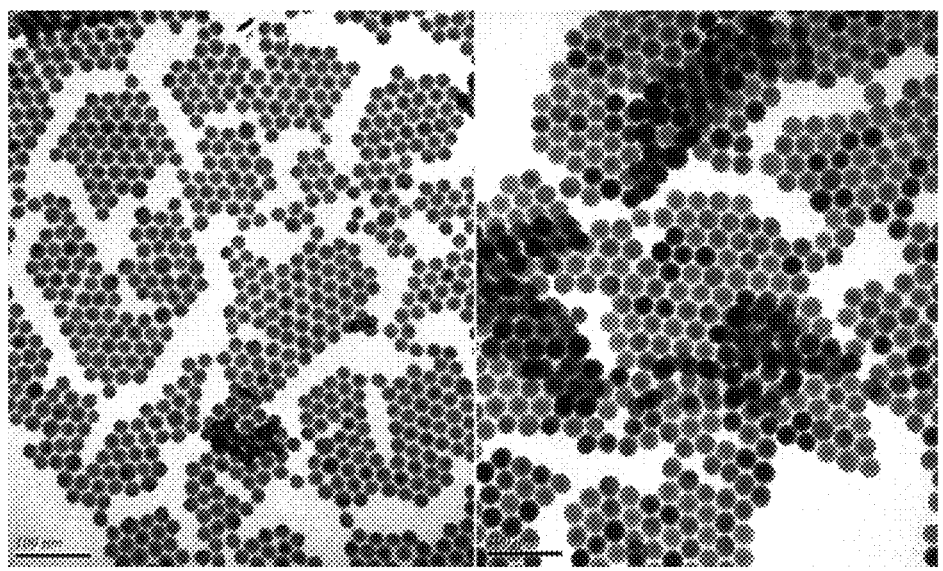
FIG. 20. β-NaYF$_4$:30%Yb,0.5%Tm (left) and the corresponding core/shell (right) UCNPs. Their respective statistical sizes are 20.5±0.8 nm and 29.2±0.9 nm.

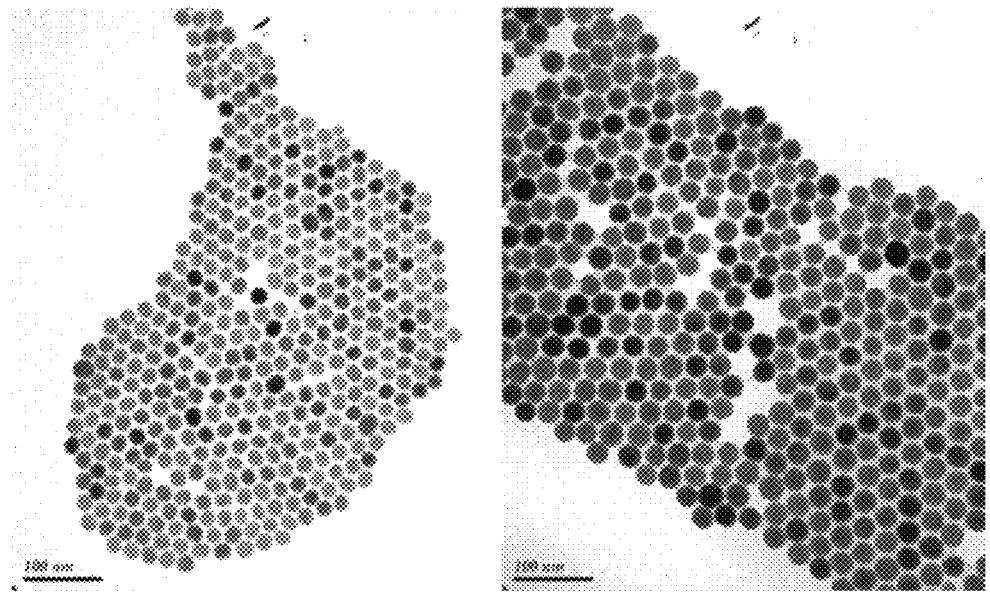
FIG. 21. β-NaYF$_4$:2%Er (left) and the corresponding core/shell (right) UCNPs. Their respective statistical sizes are 20.4±0.7 nm and 29.3±0.7 nm.
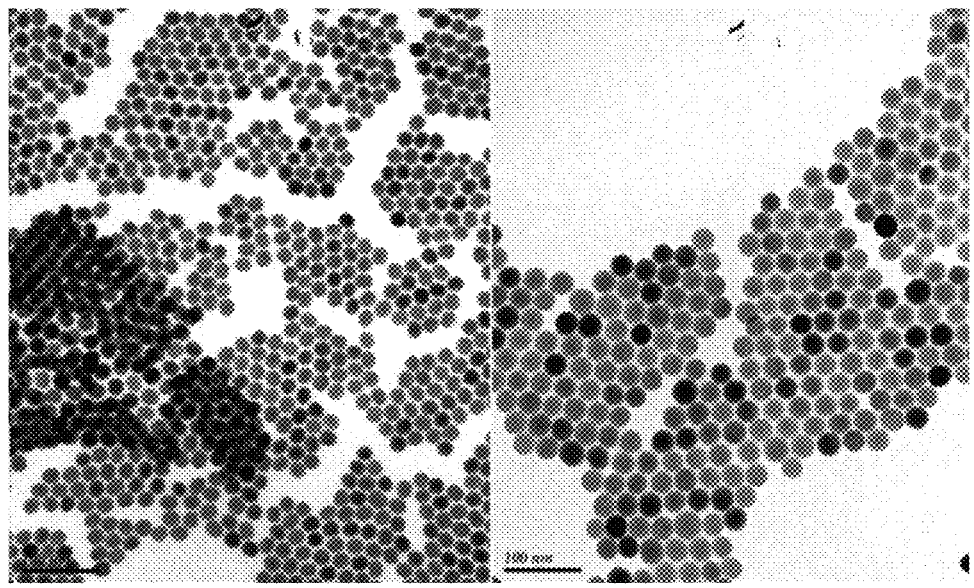
FIG. 22. β-NaYF$_4$:1%Nd (left) and the corresponding core/shell (right) UCNPs. Their respective statistical sizes are 20.7±0.5 nm and 29.9±0.8 nm.

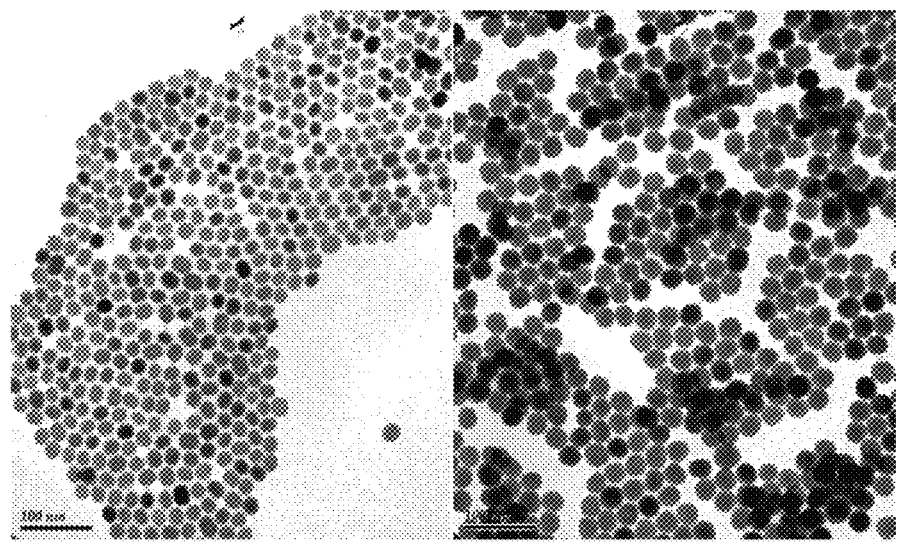
FIG. 23. β-NaYF$_4$:0.5%Nd,2%Er (left) and the corresponding core/shell (right) UCNPs. Their respective statistical sizes are 20.4±0.6 nm and 29.6±1.1 nm.

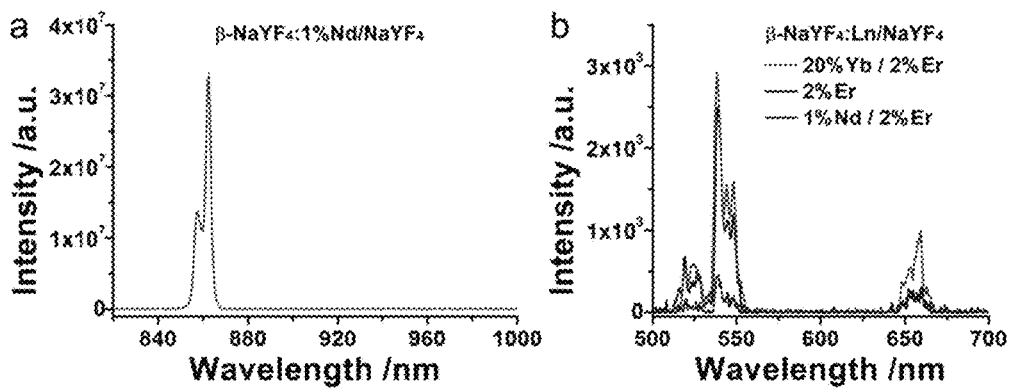

FIG. 24. (a) The Stokes emission spectra of β-NaYF$_4$:1%Nd/NaYF$_4$ NPs under 800 nm excitation. (b) The upconversion emission spectra of β-NaYF$_4$:20%Yb, 2%Er /NaYF$_4$, β-NaYF$_4$:2%Er /NaYF$_4$ and β-NaYF$_4$:1%Nd, 2%Er /NaYF$_4$ UCNPs. This figure indicates that Yb$^{3+}$ had little contribution to UCNPs photon absorbency at 800 nm, and Nd$^{3+}$ had deactivation effect to Er$^{3+}$ even at a low doping ratio. The power density of the 800 nm CW laser is 6.0 W/cm$^2$. All of the UCNPs' solutions had similar particle concentrations (0.57 μmol/L).

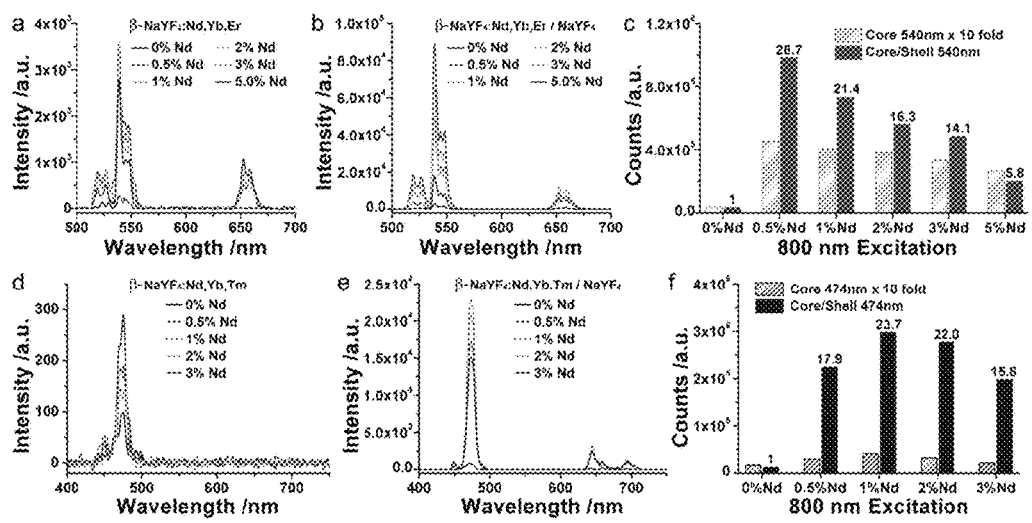

FIG. 25. The upconversion emission spectra of (a) core β-NaYF$_4$: (0-5%)Nd, 20%Yb, 2%Er, (b) core/shell β-NaYF$_4$: (0-5%)Nd, 20%Yb, 2%Er /NaYF$_4$, (d) core β-NaYF$_4$: (0-3%)Nd, 30%Yb, 0.5%Tm, and (e) core/shell β-NaYF$_4$: (0-3%)Nd, 30%Yb, 0.5%Tm /NaYF$_4$ UCNPs under 800 nm CW laser. Their corresponding emission counts are summarized in (c) and (f). The excitation power density is 6.0 W/cm$^2$. All of the UCNPs solutions had the same particle concentrations (0.57 μmol/L).

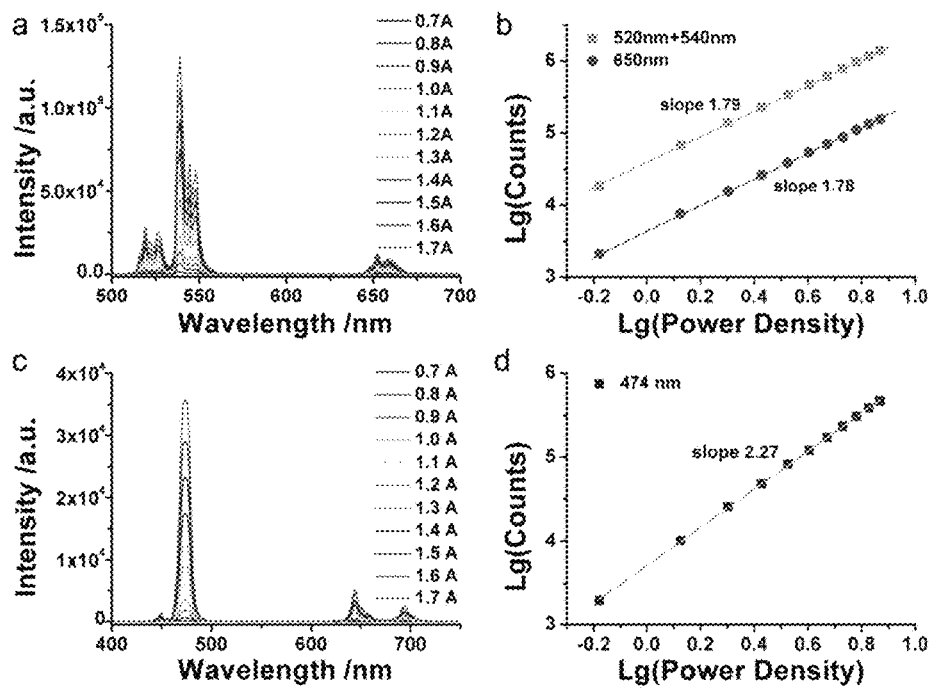
FIG. 26. (a, b) Upconversion power dependence of β-NaYF$_4$:0.5%Nd, 20%Yb, 2%Er /NaYF$_4$ and (c, d) β-NaYF$_4$:1%Nd, 30%Yb, 0.5%Tm /NaYF$_4$ (below) UCNPs under 800 nm CW laser excitation.

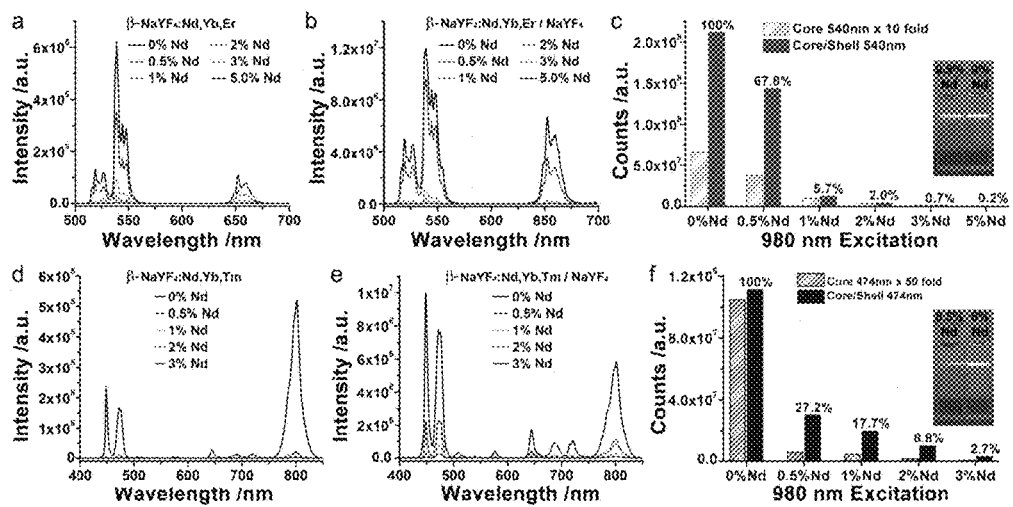

FIG. 27. The upconversion emission spectra of (a) core β-NaYF$_4$: (0-5%)Nd, 20%Yb, 2%Er, (b) core/shell β-NaYF$_4$: (0-5%)Nd, 20%Yb, 2%Er /NaYF$_4$, (d) core β-NaYF$_4$: (0-3%)Nd, 30%Yb, 0.5%Tm, and (e) core/shell β-NaYF$_4$: (0-3%)Nd, 30%Yb, 0.5%Tm /NaYF$_4$ UCNPs under 980 nm CW laser. Their corresponding emission counts were summarized in (c) and (f). The excitation power density is 23.5 W/cm$^2$. All UCNPs solutions had the same particle concentrations (0.57 μmol/L).

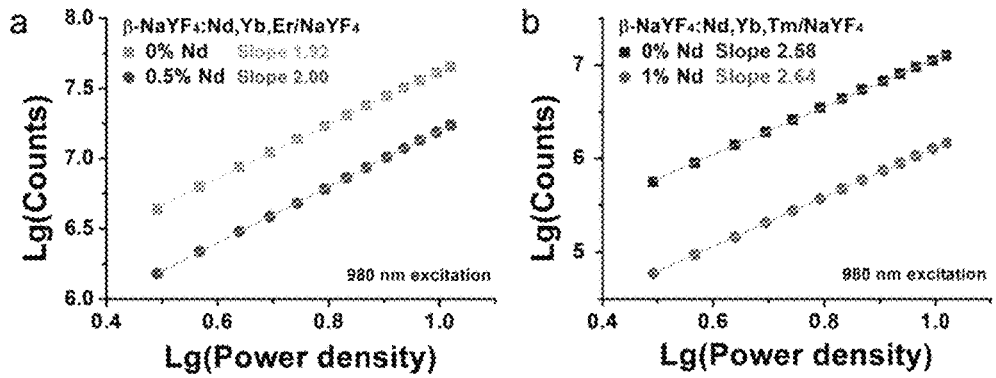

FIG. 28. Upconversion power dependence of (a) β-NaYF$_4$: (0%, 0.5%)Nd, 20%Yb, 2%Er /NaYF$_4$ and (b) β-NaYF$_4$: (0%, 1%)Nd, 30%Yb, 0.5%Tm /NaYF$_4$ UCNPs under 980 nm CW laser excitation.

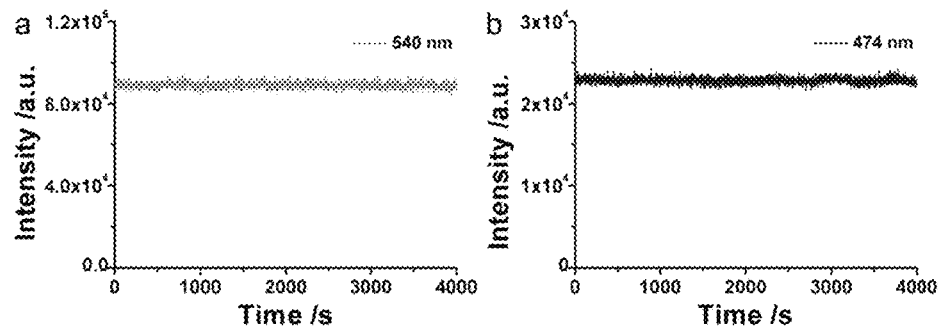

FIG. 29. The photo-stability test of β-NaYF$_4$:0.5%Nd, 20%Yb, 2%Er /NaYF$_4$ and β-NaYF$_4$:1%Nd, 30%Yb, 0.5%Tm /NaYF$_4$ UCNPs in hexane solution under 800 nm CW laser excitation (6.0 W/cm$^2$). The monitoring emission peaks are (a) $^4S_{3/2} \rightarrow {}^4I_{15/2}$ (540 nm) of Er$^{3+}$ and (b) $^1G_4 \rightarrow {}^3H_6$ (474 nm) of Tm$^{3+}$.

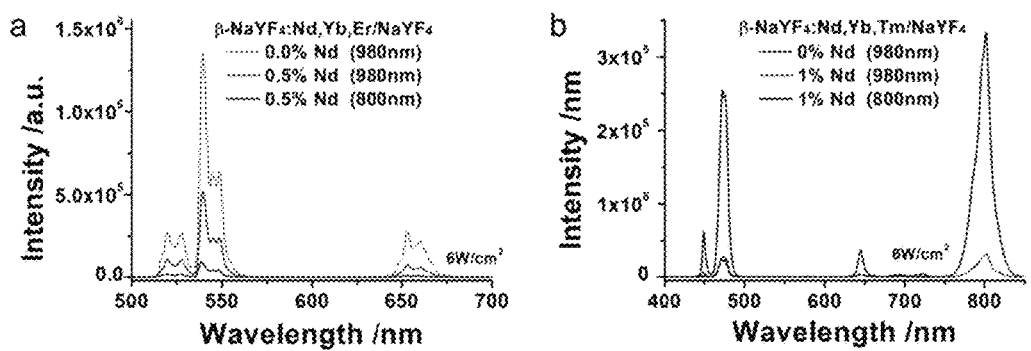

FIG. 30. Upconversion luminescence yield comparison under the same power density 980 nm and 800 nm laser excitation (6 W/cm$^2$). (a) Comparing 800 nm excited β-NaYF$_4$:0.5%Nd, 20%Yb, 2%Er /NaYF$_4$ with 980 nm excited β-NaYF$_4$:20%Yb, 2%Er /NaYF$_4$ UCNPs. (b) Comparing 800 nm excited β-NaYF$_4$:1%Nd, 30%Yb, 0.5%Tm /NaYF$_4$ with 980 nm excited β-NaYF$_4$:30%Yb, 0.5%Tm /NaYF$_4$ UCNPs. All of the UCNPs' solutions had the same particle concentrations (0.57 μmol/L).

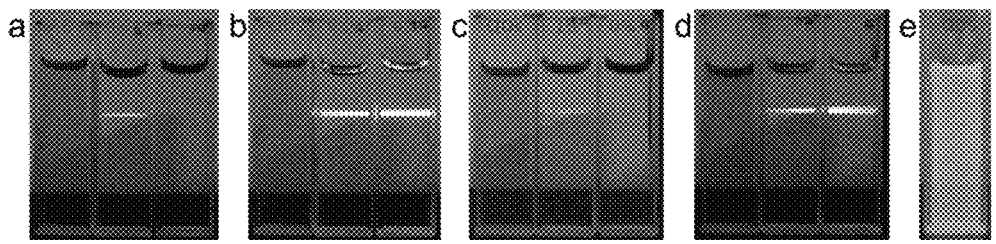

FIG. 31. Photographs of visible luminescence signals from core/shell UCNPs and CdSe/ZnS QDs solutions. The solutions of QDs, β-NaYF$_4$: (0%, 0.5%)Nd, 20%Yb, 2%Er /NaYF$_4$ UCNPs under (a) 6 W/cm$^2$ of 800 nm CW laser and (b) 23.5 W/cm$^2$ of 980 nm CW laser excitation. The solutions of QDs, β-NaYF$_4$: (0%, 1%) Nd, 30%Yb, 0.5%Tm /NaYF$_4$ UCNPs under (c) 6 W/cm$^2$ of 800 nm CW laser and (d) 23.5 W/cm$^2$ of 980 nm CW laser excitation. (e) The solutions of CdSe/ZnS core/shell QDs under 362 nm UV lamp excitation.

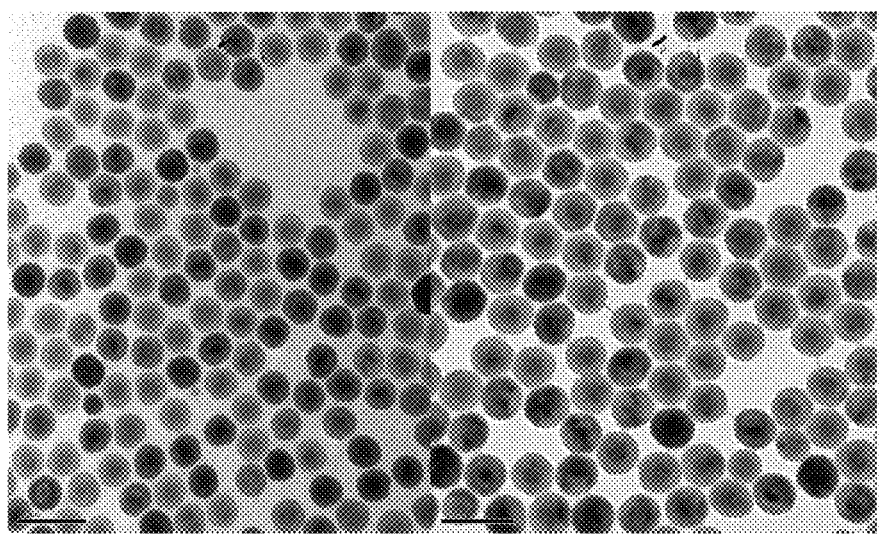

FIG. 32 TEM images of core-shell (left) and core-shell-shell (right)

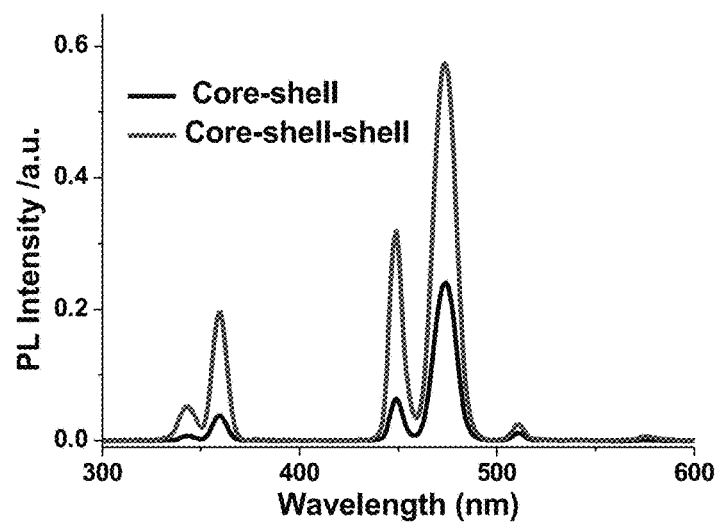
FIG. 33 The emission spectra of core-shell and core-shell-shell UCNPs under excitation of an 800 nm CW diode laser.

COMPOSITIONS AND METHODS FOR UPCONVERTING LUMINESCENCE WITH ENGINEERED EXCITATION AND APPLICATIONS THEREOF

PRIORITY CLAIMS AND RELATED APPLICATIONS

This application is the U.S. national phase of and claims priority to PCT/US14/12437, filed Jan. 22, 2014, which claims the benefit of priority from U.S. Provisional Application Ser. No. 61/755,424, filed on Jan. 22, 2013, the entire content of each of which is incorporated herein by reference in its entirety.

TECHNICAL FIELDS OF THE INVENTION

The invention generally relates to materials and methods for generating and/or utilizing upconverting luminescence. More particularly, the invention relates to novel materials and compositions (e.g., nanoparticles) and related methods of preparation and use that enable upconverting luminescence with an efficient and optimized excitation (e.g., at about 800 nm).

BACKGROUND OF THE INVENTION

Upconversion nanoparticles (UCNPs) have recently emerged as a new class of materials with potential applications in a wide-range of fields, such as biosensing, chemical sensing, in vivo imaging, drug delivery, photodynamic therapy and photoactivation. (Zhan, et al. 2011 *Acs Nano* 5, 3744; Wang, et al. 2005 *Angew Chem Int Edit* 44, 6054; Achatz, et al. 2011 *Angew Chem Int Edit* 50, 260; Liu, et al. 2011 *Acs Nano* 5, 8040; Liu, et al. 2011 *J Am Chem Soc* 133, 17122; Chen, et al. 2012 *Acs Nano* 6, 8280; Lim, et al. 2006 *Nano Lett* 6, 169; Wang, et al. 2011 *Biomaterials* 32, 1110; Hou, et al. 2011 *Adv Funct Mater* 21, 2356; Tian, et al. 2012 *Adv Mater* 24, 1226; Shan, et al. 2011 *Adv Funct Mater* 21, 2488; Zhang, et al. 2007 *J Am Chem Soc* 129, 4526; Jayakumar, et al. 2012 *Natl Acad Sci USA* 109, 8483; Yang, et al. 2012 *Angew Chem Int Edit* 51, 3125; Yan, et al. 2012 *J Am Chem Soc* 134, 16558; U.S. Pat. Nos. 7,332,344; 7,790,392; 7,501,092; 8,088,631.)

Upconverting luminescence refers to an anti-Stokes type process in which the sequential absorption of two or more photons leads to the emission of light at shorter wavelength (e.g., ultraviolet, visible, and near-infrared) than the excitation wavelength. For instance, Lanthanide ion ($Ln^{3+}$) doped UCNPs are able to absorb near-infrared (NIR) photons and convert such low energy excitation into shorter wavelength emissions. (Haase, et al. 2011 *Angew Chem Int Edit* 50, 5808.) Utilizing long-lived, ladder-like energy levels of $Ln^{3+}$, the intensity of anti-Stokes luminescence of UCNPs is orders of magnitude more potent compared with those of conventional synthetic dyes or quantum dots (QDs). (Wang, et al. 2009 *Chem Soc Rev* 38, 976; U.S. Provisional Appl. No. 61/675,019 by Han, et al.; U.S. Provisional Appl. No. 61/653,406 by Han, et al.; PCT/US13/42555 by Han, et al. filed May 24, 2013.)

Challenges remain, however, that hamper the wide use of UCNPs. For example, a major limitation of the most commonly used $Yb^{3+}$-sensitized UCNPs is their physically unalterable excitation band centered at 980 nm (the peak absorption of $Yb^{3+}$ ions), overlapping with the maximum absorption peak of water molecules (FIG. 1). Because cells and tissues withhold 980 nm radiation and concomitantly induce heat damages, this becomes problematic for application of UCNPs in water-rich biological systems. (McNichols, et al. 2004 *Laser Surg Med* 34, 48; Nam, et al. 2011 *Angew Chem Int Edit* 50, 6093.) In particular, the heating effect is likely more severe where greater power density and longer-term irradiation are required, such as in single nanoparticle imaging or longitudinally deep tissue imaging.

While extensive research has resulted in continued progress in the modulation of UCNP's emissions, for example, via composing proper dopants/matrix or FRET process, few studies have focused on engineering the excitation of UCNPs. (Tian, et al. 2012 *Adv Mater* 24, 1226; Wang, et al. 2011 *Nat Mater* 10, 968; Li, et al. 2008 *Adv Mater* 20, 4765; Yi, et al. 2011 *Chem Mater* 23, 2729; Chan, et al. 2012 *Nano Lett* 12, 3839; Heer, et al. 2003 *Angew Chem Int Edit* 42, 3179; Zhan, et al. 2011 *Acs Nano* 5, 3744.) A recent report showed the use of an alternative excitation peak at 915 nm in $Yb^{3+}$-sensitized cubic phase (a) $NaYF_4$:Ln UCNPs. This excitation peak, however, is still well within the regime of intrinsic absorption of $Yb^{3+}$ dopants, which partially overlaps with the absorption peak of water. Another report used dye-sensitized UCNPs under 800 nm excitation, in which an antenna dye was used to stimulate the $Yb^{3+}$—$Er^{3+}$ upconverting process via the fluorescence resonance energy transfer (FRET) mechanism. (Zou, et al. 2012 *Nat Photonics* 6, 560.) This FRET-based approach, however, is limited to the organic media with the synthetic dyes susceptible to photobleaching. Additionally, the FRET process is restricted by the distance between the organic molecules and the UCNPs.

Thus, un-met needs continue to exist for novel compositions and methods that enable upconverting luminescence with efficient excitation away from peak absorption of water, preferably near a minimum of water absorption.

SUMMARY OF THE INVENTION

The invention provides novel upconverting luminescence materials (e.g., UCNPs) and methods that have constitutional excitation engineered to optimize at about 800 nm, which is not only well away from peak absorption of water, but also is ideally situated at a local minimum of water absorption. A unique class of cascade sensitized tri-doped UCNPs with a biocompatible 800 nm excitable property are disclosed herein, for example, tri-doped $\beta$-$NaYF_4$:Nd,Yb, Er(Tm)/$NaYF_4$ UCNPs, which employ $Nd^{3+}$ as 800 nm photon sensitizer and $Yb^{3+}$ as bridging ions, affording strong green or blue upconversion emissions without photobleaching. The UCNPs of the invention are preferably configured, for example, in a $\beta$-$NaYF_4$:Yb, Er(Tm)/$NaYF_4$, Yb, Nd core/shell or a $\beta$-$NaYF_4$:Yb, Er(Tm)/$NaYF_4$, Yb, Nd/$NaYF_4$ core/shell/shell architects. These UCNPs are amendable to physically engineering the excitation wavelengths of upconversion nanoparticles and can be employed in a wide range of applications, for example, in biological sensing, chemical sensing, in vitro or in vivo imaging (e.g., tumor-targeted imaging, multimodal imaging), drug delivery, photodynamic therapy, photoactivation, photovoltaic and solar cells, photocatalysts, and 3-D displays.

In one aspect, the invention generally relates to an upconversion luminescence material. The upconversion luminescence material includes: (1) a first Lanthanide, $Ln_{(i)}$, having a mol % from about 0.1% to about 10% (e.g., 0.2%, 0.5%, 1%, 1.5%, 2%, 2.5%, 3%, 3.5%, 4%, 4.5%, 5%, 6%, 7%, 8%, 9%); (2) a second Lanthanide ion, $Ln_{(j)}$, having a mol % from about 10% to about 80% (e.g., 15%, 20%, 25%, 30%, 35%, 40%, 45%, 50%, 55%, 60%, 65% 70%, 75%); and (3) a third Lanthanide ion, $Ln_{(k)}$, having a mol % from about 0.1 to about 10% (e.g., 0.2%, 0.5%, 1%, 1.5%, 2%, 2.5%, 3%, 3.5%, 4%, 4.5%, 5%, 6%, 7%, 8%, 9%). The upconversion luminescence material is characterized by a constitutional excitation peak substantially away from 980 nm. In certain preferred embodiments, the upconversion luminescence material is characterized by a constitutional excitation peak at about 800 nm, the upconversion luminescence material includes $\beta$-NaYF$_4$, and Ln$_{(i)}$ is Nd; Ln$_{(j)}$ is Yb; and Ln$_{(k)}$ is Er or Tm.

In another aspect, the invention generally relates to a biocompatible upconversion luminescence nanoparticle, which include: a tri-doped core of $\beta$-NaYF$_4$: Ln$_{(i)}$,Ln$_{(j)}$, Ln$_{(k)}$; and an epitaxial shell of $\beta$-NaYF$_4$, wherein Ln$_{(i)}$ is Nd; Ln$_{(j)}$ is Yb; and Ln$_{(k)}$ is Er, Ho or Tm.

In yet another aspect, the invention generally relates to a biocompatible upconversion luminescence nanoparticle, which includes: a core of $\beta$-NaYF$_4$: Ln$_{(j)}$, Ln$_{(k)}$; an epitaxial inner shell of $\beta$-NaYF$_4$: Ln$_{(i)}$,Ln$_{(j)}$,Ln$_{(k)}$; and an epitaxial outer shell of $\beta$-NaYF$_4$. Ln$_{(i)}$ is Nd; Ln$_{(j)}$ is Yb; and Ln$_{(k)}$ is Er or Tm.

In yet another aspect, the invention generally relates to a sensing probe for detecting a target molecule in a sample. The sensing probe includes an upconversion luminescence material and/or a biocompatible upconversion luminescence nanoparticle disclosed herein.

In yet another aspect, the invention generally relates to a method for detecting a target molecule in a sample. The method includes: providing a sensing probe comprising an upconversion luminescence nanoparticle having a constitutional excitation peak at about 800 nm, wherein the sensing probe is capable of association with the target molecule; contacting the sensing probe with a sample to be tested for the presence of the target molecule under a condition such that if the target molecule is present the sensing probe becomes associated with the target molecule; exciting the sensing probe with an excitation at about 800 nm; and detecting an emission at a shorter wavelength than 800 nm to determining the presence of the target molecule.

In yet another aspect, the invention generally relates to an imaging system comprising an upconversion luminescence material and/or an upconversion luminescence nanoparticle of the invention.

In yet another aspect, the invention generally relates to a photonics system comprising an upconversion luminescence material and/or a upconversion luminescence nanoparticle of the invention.

BRIEF DESCRIPTION OF THE FIGURES

FIG. 1. Spectra profiles showing tissue optical window. The extinction coefficient of water at 800 nm is about 20 timers lower than that at 980 nm.

FIG. 2. Upconversion process of Nd$^{3+}$→Yb$^{3+}$→Er$^{3+}$ (Tm$^{3+}$) tri-dopants system with 800 nm excitation.

FIG. 3. Transmission Electron Microscopy (TEM) images of (a) $\beta$-NaYF$_4$:0.5% Nd,20% Yb,2% Er, (b) $\beta$-NaYF$_4$:Nd,Yb,Er/NaYF$_4$, (c)$\beta$-NaYF$_4$:1% Nd,30% Yb,0.5% Tm and (d) $\beta$-NaYF$_4$:Nd,Yb,Tm/NaYF$_4$ UCNPs. (e) The X-ray Diffraction (XRD) patterns of four samples and index data of $\beta$-NaYF$_4$.

FIG. 4. The upconverting emission spectra and emission counts summary of (a, b) $\beta$-NaYF$_4$:(0-5%)Nd, 20% Yb, 2% Er/NaYF$_4$ and (c, d) $\beta$-NaYF$_4$:(0-3%)Nd, 30% Yb, 0.5% Tm/NaYF$_4$ UCNPs. The measurement was applied under 800 nm CW laser excitation (6.0 W/cm$^2$) using the concentration normalized UCNPs solutions. The upconverting luminescent pictures were inserted in (b, d) with the laser path labeled.

FIG. 5. The upconverting emission spectra and emission counts of (a, b, c) $\beta$-NaYF$_4$:Nd,Yb,Er core and core/shell UCNPs, (d, e, f) $\beta$-NaYF$_4$:Nd,Yb,Tm core and core/shell UCNPs under 800 nm CW laser excitation (6.0 W/cm$^2$). All of the UCNPs solutions have the same particle concentrations.

FIG. 6. (a) Hydrodynamics size, (b) potential distributions of PAA modified $\beta$-NaYF$_4$:0.5% Nd, 20% Yb, 2% Er/NaYF$_4$ and $\beta$-NaYF$_4$:1% Nd, 30% Yb, 0.5% Tm/NaYF$_4$ UCNPs, and (c) 800 nm excited upconverting luminescence.

FIG. 7. The output power of (a) the 800 nm CW laser and (b) the 980 nm laser under different operating laser currents.

FIG. 8. $\beta$-NaYF$_4$:0.5% Nd,20% Yb,2% Er (left) and the corresponding core/shell (right) UCNPs. Their respective statistical sizes are 20.2±1.6 nm and 29.5±1.0 nm.

FIG. 9. $\beta$-NaYF$_4$:1% Nd,20% Yb,2% Er (left) and the corresponding core/shell (right) UCNPs. Their respective statistical sizes are 20.4±0.6 nm and 29.2±0.9 nm.

FIG. 10. $\beta$-NaYF$_4$:2% Nd,20% Yb,2% Er (left) and the corresponding core/shell (right) UCNPs. Their statistical sizes are 20.3±1.2 nm and 29.0±1.3 nm.

FIG. 11. $\beta$-NaYF$_4$:3% Nd,20% Yb,2% Er (left) and the corresponding core/shell (right) UCNPs. Their respective statistical sizes are 19.7±0.7 nm and 29.3±1.2 nm.

FIG. 12. $\beta$-NaYF$_4$:5% Nd,20% Yb,2% Er (left) and the corresponding core/shell (right) UCNPs. Their respective statistical sizes are 19.9±1.4 nm and 28.8±0.9 nm.

FIG. 13. $\beta$-NaYF$_4$:1% Nd,40% Yb,2% Er (left) and the corresponding core/shell (right) UCNPs. Their respective statistical sizes are 21.2±1.0 nm and 29.4±1.4 nm.

FIG. 14. $\beta$-NaYF$_4$:1% Nd,60% Yb,2% Er (left) and the corresponding core/shell (right) UCNPs. Their respective statistical sizes are 20.5±0.8 nm and 29.1±2.3 nm.

FIG. 15. $\beta$-NaYF$_4$:20% Yb,2% Er (left) and the corresponding core/shell (right) UCNPs. Their respective statistical sizes are 20.7±0.7 nm and 29.8±0.5 nm.

FIG. 16. $\beta$-NaYF$_4$:0.5% Nd,30% Yb,0.5% Tm (left) and the corresponding core/shell (right) UCNPs. Their respective statistical sizes are 20.0±1.1 nm and 29.1±0.5 nm.

FIG. 17. $\beta$-NaYF$_4$:1% Nd,30% Yb,0.5% Tm (left) and the corresponding core/shell (right) UCNPs. Their respective statistical sizes are 20.5±1.9 nm and 29.1±1.2 nm.

FIG. 18. $\beta$-NaYF$_4$:2% Nd,30% Yb,0.5% Tm (left) and the corresponding core/shell (right) UCNPs. Their respective statistical sizes are 20.1±1.7 nm and 29.3±1.8 nm.

FIG. 19. $\beta$-NaYF$_4$:1% Nd,60% Yb,0.5% Tm (left) and the corresponding core/shell (right) UCNPs. Their respective statistical sizes are 20.4±1.3 nm and 29.8±1.9 nm.

FIG. 20. $\beta$-NaYF$_4$:30% Yb,0.5% Tm (left) and the corresponding core/shell (right) UCNPs. Their respective statistical sizes are 20.5±0.8 nm and 29.2±0.9 nm.

FIG. 21. $\beta$-NaYF$_4$:2% Er (left) and the corresponding core/shell (right) UCNPs. Their respective statistical sizes are 20.4±0.7 nm and 29.3±0.7 nm.

FIG. 22. $\beta$-NaYF$_4$:1% Nd (left) and the corresponding core/shell (right) UCNPs. Their respective statistical sizes are 20.7±0.5 nm and 29.9±0.8 nm.

FIG. 23. $\beta$-NaYF$_4$:0.5% Nd,2% Er (left) and the corresponding core/shell (right) UCNPs. Their respective statistical sizes are 20.4±0.6 nm and 29.6±1.1 nm.

FIG. 24. (a) The Stokes emission spectra of $\beta$-NaYF$_4$:1% Nd/NaYF$_4$NPs under 800 nm excitation. (b) The upconversion emission spectra of $\beta$-NaYF$_4$:20% Yb, 2% Er/NaYF$_4$, $\beta$-NaYF$_4$:2% Er/NaYF$_4$ and $\beta$-NaYF$_4$:1% Nd, 2%

Er/NaYF$_4$ UCNPs. This figure indicates that Yb$^{3+}$ had little contribution to UCNPs photon absorbency at 800 nm, and Nd$^{3+}$ had deactivation effect to Er$^{3+}$ even at a low doping ratio. The power density of the 800 nm CW laser is 6.0 W/cm$^2$. All of the UCNPs' solutions had similar particle concentrations (0.57 μmol/L).

FIG. 25. The upconversion emission spectra of (a) core β-NaYF$_4$: (0-5%)Nd, 20% Yb, 2% Er, (b) core/shell β-NaYF$_4$: (0-5%)Nd, 20% Yb, 2% Er/NaYF$_4$, (d) core β-NaYF$_4$: (0-3%)Nd, 30% Yb, 0.5% Tm, and (e) core/shell β-NaYF$_4$: (0-3%)Nd, 30% Yb, 0.5% Tm/NaYF$_4$ UCNPs under 800 nm CW laser. Their corresponding emission counts are summarized in (c) and (f). The excitation power density is 6.0 W/cm$^2$. All of the UCNPs solutions had the same particle concentrations (0.57 μmol/L).

FIG. 26. (a, b) Upconversion power dependence of β-NaYF$_4$:0.5% Nd, 20% Yb, 2% Er/NaYF$_4$ and (c, d) β-NaYF$_4$:1% Nd, 30% Yb, 0.5% Tm/NaYF$_4$ (below) UCNPs under 800 nm CW laser excitation.

FIG. 27. The upconversion emission spectra of (a) core β-NaYF$_4$: (0-5%)Nd, 20% Yb, 2% Er, (b) core/shell β-NaYF$_4$: (0-5%)Nd, 20% Yb, 2% Er/NaYF$_4$, (d) core β-NaYF$_4$: (0-3%)Nd, 30% Yb, 0.5% Tm, and (e) core/shell β-NaYF$_4$: (0-3%)Nd, 30% Yb, 0.5% Tm/NaYF$_4$ UCNPs under 980 nm CW laser. Their corresponding emission counts were summarized in (c) and (f). The excitation power density is 23.5 W/cm$^2$. All UCNPs solutions had the same particle concentrations (0.57 μmol/L).

FIG. 28. Upconversion power dependence of (a) β-NaYF$_4$: (0%, 0.5%)Nd, 20% Yb, 2% Er/NaYF$_4$ and (b) β-NaYF$_4$: (0%, 1%)Nd, 30% Yb, 0.5% Tm/NaYF$_4$ UCNPs under 980 nm CW laser excitation.

FIG. 29. The photo-stability test of β-NaYF$_4$:0.5% Nd, 20% Yb, 2% Er/NaYF$_4$ and β-NaYF$_4$:1% Nd, 30% Yb, 0.5% Tm/NaYF$_4$ UCNPs in hexane solution under 800 nm CW laser excitation (6.0 W/cm$^2$). The monitoring emission peaks are (a)$^4S_{3/2} \rightarrow {}^4I_{15/2}$ (540 nm) of Er$^{3+}$ and (b) $^1G_4 \rightarrow {}^3H_6$ (474 nm) of Tm$^{3+}$.

FIG. 30. Upconversion luminescence yield comparison under the same power density 980 nm and 800 nm laser excitation (6 W/cm$^2$). (a) Comparing 800 nm excited β-NaYF$_4$:0.5% Nd, 20% Yb, 2% Er/NaYF$_4$ with 980 nm excited β-NaYF$_4$:20% Yb, 2% Er/NaYF$_4$ UCNPs. (b) Comparing 800 nm excited β-NaYF$_4$:1% Nd, 30% Yb, 0.5% Tm/NaYF$_4$ with 980 nm excited β-NaYF$_4$:30% Yb, 0.5% Tm/NaYF$_4$ UCNPs. All of the UCNPs' solutions had the same particle concentrations (0.57 μmol/L).

FIG. 31. Photographs of visible luminescence signals from core/shell UCNPs and CdSe/ZnS QDs solutions. The solutions of QDs, β-NaYF$_4$: (0%, 0.5%)Nd, 20% Yb, 2% Er/NaYF$_4$ UCNPs under (a) 6 W/cm$^2$ of 800 nm CW laser and (b) 23.5 W/cm$^2$ of 980 nm CW laser excitation. The solutions of QDs, β-NaYF$_4$: (0%, 1%) Nd, 30% Yb, 0.5% Tm/NaYF$_4$ UCNPs under (c) 6 W/cm$^2$ of 800 nm CW laser and (d) 23.5 W/cm$^2$ of 980 nm CW laser excitation. (e) The solutions of CdSe/ZnS core/shell QDs under 362 nm UV lamp excitation.

FIG. 32 TEM images of a β-NaYF$_4$: Yb, Er(Tm)/NaYF$_4$, Yb, Nd core/shell or a β-NaYF$_4$: Yb, Er(Tm)/NaYF$_4$, Yb, Nd/NaYF$_4$ core/shell/shell.

FIG. 33 The emission spectra of β-NaYF$_4$: Yb, Er(Tm)/NaYF$_4$, Yb, Nd core/shell or a β-NaYF$_4$: Yb, Er(Tm)/NaYF$_4$, Yb, Nd/NaYF$_4$ core-shell-shell UCNPs under excitation of an 800 nm CW diode laser.

DESCRIPTION OF THE INVENTION

This invention provides a unique class of cascade sensitized tri-doped UCNPs with a biocompatible 800 nm excitable property, corresponding to a local minimum of water absorption. Tri-doped β-NaYF$_4$:Nd,Yb,Er(Tm)/NaYF$_4$UCNPs, for example, employ Nd$^{3+}$ as 800 nm photon sensitizer and Yb$^{3+}$ as bridging ions, resulting in strong green or blue upconversion emissions.

FIG. 1 shows spectra tissue optical window. Commonly used Yb$^3$-sensitized UCNPs have their peak absorption of Yb$^{3+}$ ions (excitation) centered at 980 nm, which overlaps with the maximum absorption peak of water molecules. In contrast, the extinction coefficient of water at 800 nm, the local minima of water absorption, is about 20 timers lower than that at 980 nm. Therefore, 800 nm has been considered to be the ideal excitation wavelength with the least impact on biological tissues. (Kobayashi, et al. 2010 Chem Rev 110, 2620; Xie, et al. 2012 Nat Mater 11, 842.)

The present invention discloses an unconventional strategy. Rather than employing dye-sensitization, the invention provides upconversion materials and UCNPs with constitutional excitation specifically engineered to about 800 nm. This approach paves the way for broad applications of a new generation of UCNPs with much-improved biocompatibility and exciting penetrability.

Unlike the single-type sensitizer (e.g., Yb$^{3+}$) in typical dual doped UCNPs, tri-doped cascade sensitized UCNPs of the invention employ a primary sensitizer (e.g., Nd$^{3+}$) and a secondary sensitizer (e.g., Yb$^{3+}$). The probable upconversion mechanism with Nd$^{3+}$ sensitizing and Yb$^{3+}$ transferring is presented in FIG. 2. Nd$^{3+}$ ions take the role of absorbing photons at 800 nm, while the Yb$^{3+}$ ions act as bridging ions for the energy transfer from the Nd$^{3+}$ ions to the emitters, Er$^{3+}$ or Tm$^{3+}$.

UCNPs prepared according to the methods of the invention, for example, Nd$^{3+}$/Yb$^{3+}$/Er$^{3+}$(Tm$^{3+}$) tri-doped core/shell β-NaYF$_4$ UCNPs prepared via the solution synthesis, displayed robust upconverting emission with 800 nm continuous-wave (CW) laser excitation. The presence of a small quantity of Nd$^{3+}$ (doping ratio≤1%) in the tri-doped systems is important for the purpose of sensitizing at 800 nm, resulting in more than 20-fold stronger emissions than the traditional dual-dopants Yb$^{3+}$-sensitized system.

Significantly, with surface modification, the tri-doped UCNPs dispersed in water still exhibit strong 800 nm excitable luminescence, which is visible to the naked eye in ambient indoor light. Along with their non-bleaching advantage, such tri-doped UCNPs are a new and promising class of anti-Stokes luminescent probes using biocompatible 800 nm excitations.

More specifically, Nd$^{3+}$ is known for its optical activity in the NIR region, and its $^4I_{9/2} \rightarrow {}^4F_{5/2}$ transition offers a strong absorption at ca. 800 nm. (Guyot, et al. 1995 Phys Rev B Condens Matter 51, 784.) It has been reported that the excited Nd$^{3+}$ on the $^4F_{5/2}$ level can relax to the lower $^4F_{312}$ level and then sensitize the ground state Yb$^{3+}$ ions nearby via resonance energy transfer. (Balda, et al. 2010 Opt Express 18, 13842.) For example, previously, in glass ceramics and bulk crystal materials, spectroscopic physics studies have experimentally validated the feasiblity of such a 800 nm pumped upconversion process. (Lu, et al. 2007 J Lumin 126, 677; Chen, et al. 2007 Opt Lett 32, 3068; Li, et al. 2009 J Appl Phys 105, 013536.) However, unlike colloidal dispersible nanoparticles, due to their size dimensions, uncontrolled morphology, low upconversion efficiency, and surface chemistry, these bulk materials are rather problematic for biological usages. (Auzel 2004 Chem Rev 104, 139; Lin, et al. 2010 J Appl Phys 107; Camargo, et al. 2004 J Appl Phys 95, 2135.) Yet, it has been a great challenge to achieve Nd$^{3+}$ sensitized strong upconversion inside small colloidal monodispersible UCNPs. The possible reasons for this are as follows: (1) Compared with the $Yb^{3+}/Er^{3+}$ or $Yb^{3+}/Tm^{3+}$ dual-dopants combination, the cascade multiple-step resonance energy transfer (i.e., $Nd^{3+} \rightarrow Yb^{3+} \rightarrow Er^{3+}$ or $Tm^{3+}$) of the tri-dopant upconversion systems suffer from a greater surface quenching risk in the colloidal UCNPs. (2) Compared to the simple excited state of $Yb^{3+}$, the excited $Nd^{3+}$ states are rather complicated for a primary sensitizer, and this may lead to more severe deleterious deactivation of the excited emitters via cross-relaxations.

The invention addresses the first challenge by novel configurations of the UCNPs, for example by way of epitaxial core/shell or core/shell/shell strategies. Due to the advantage of low phonon energy, a hexagonal phased (β)-$NaYF_4$ matrix was selected. (Haase, et al. 2011 *Angew Chem Int Edit* 50, 5808; Wang, et al. 2009 *Chem Soc Rev* 38, 976.) A major deleterious factor in regard to luminescence emission of colloidal UCNPs is the energy traps on their surface, which include sublattice defects and external deactivators (e.g., ligands). The calculation for a 20 nm β-$NaYF_4$:Ln nanosphere revealed that 29% of the total $Ln^{3+}$ dopants are exposed on the particle surface and are susceptible to such energy deactivation. Compared to $Yb^{3+}/Er^{3+}$ and $Yb^{3+}/Tm^{3+}$ dual-dopant systems, the tri-dopant's cascade sensitized upconversion undergoes additional energy transfer steps, i.e. the initial steps of $Nd^{3+} \rightarrow Yb^{3+}$ sensitizing. If each $Ln^{3+}$ has the same intralattice deactivation probability, the overall yield of $Nd^{3+} \rightarrow Yb^{3+} \rightarrow Er^{3+}(Tm^{3+})$ upconversion will be exponentially lower than that of $Yb^{3+} \rightarrow Er^{3+}(Tm^{3+})$. Thus, shielding energy deactivators from UCNP surface dopants is essential in the cascade sensitized upconversion.

The typically adopted strategy of UCNPs surface passivation is that of developing an inert shell free of dopants. (Qian, et al. 2008 *Langmuir* 24, 12123; Yi, et al. 2007 *Chem Mater* 19, 341.) Under the protection of an epitaxial growth β-$NaYF_4$ shell, the UCNPs surface related quenching can be largely suppressed, and the efficiency differences between our tri-dopants UCNPs and the classical dual-dopant UCNPs are shortened. (Su, et al. 2012 *J Am Chem Soc* 134,20849.)

The solution-phase synthesis of β-$NaYF_4$:Nd,Yb,Er(Tm)/$NaYF_4$ core/shell UCNPs employed a modified trifluoroacetates thermolysis method. (Mai, et al. 2006 *J Am Chem Soc* 128, 6426.) It is worthy of noting that it is the first time that β-$NaYF_4$:Ln/$NaYF_4$ core/shell UCNPs were successfully prepared with the trifluoroacetates thermolysis method. In brief, α-$NaYF_4$:Ln was first prepared as the intermediate UCNPs by thermo-decomposition of trifluoroacetate precursors in high-boiling point solvents at 300° C. This was followed by α→β phase-transition with additional sodium trifluoroacetate at a higher crystallization temperature (325° C.). After purification, the as-prepared β-$NaYF_4$:Ln UCNPs were reacted with fresh $CF_3COONa$ and $Y(CF_3COO)_3$ for epitaxial growth of β-$NaYF_4$ shell via seed-mediated crystallization.

It has been reported that epitaxial shell thickness shows a direct proportion to the emission enhancing folds on core/shell UCNPs. (Johnson, et al. 2012 *J Am Chem Soc* 134, 11068.) Since only a sufficient epitaxial growth can produce high-crystallized shell to protect UCNP core in a compact manner, we set 1:2 ratio as the precursor's input ratio for the UCNP core and shell components. As shown in the TEM images from FIG. 3 and FIGS. 8-23, the β-$NaYF_4$:Nd,Yb,Er(Tm) core UCNPs have a uniform nanosphere morphology with an average diameter of 20 nm, and the core/shell UCNPs have an average diameter of 29 nm. The calculated volume ratio of core and shell is ca. 1:2.05, well consistent with the input ratio. The XRD patterns of core and core/shell UCNPs confirm the presence of a pure β phase structure, while the core/shell UCNPs show slightly narrower peak bandwidths.

The invention addresses the second challenge by optimizing the primary sensitizer $Nd^{3+}$ doping ratio in the tri-dopant upconversion system. Distinct from single excited state of $Yb^{3+}$, $Nd^{3+}$ has abundant energy levels that may deactivate emitter dopants rather than sensitize them. In order to weaken such deleterious deactivation, $Nd^{3+}$ should be kept at a sufficient distance away from $Er^{3+}(Tm^{3+})$. Since all $Ln^{3+}$ dopants are considered to be homogenously dispersed inside β-$NaYF_4$ matrix, their mean distances have an inverse proportion to their concentrations. Thus, for optimization, $Nd^{3+}$ was adjusted to a relatively low doping concentration (0.5-5%) inside UCNP core. (Chen, et al. 2012 *Acs Nano* 6, 2969.) At the same time, for the other two dopant concentrations inside the UCNPs core, the classical dual-dopants optimal ratios were followed, i.e. 20%/2% for $Yb^{3+}/Er^{3+}$, and 30%/0.5% for $Yb^{3+}/Tm^{3+}$. (Haase, et al. 2011 *Angew Chem Int Edit* 50, 5808; Wang, et al. 2009 *Chem Soc Rev* 38, 976.)

The upconvesion spectra were characterized on a SPEX Fluoromax-3 spectrofluorimeter equipped with an 800 nm CW laser. All of the as-synthesized core and core/shell UCNPs were dispersed in hexane to form transparent colloidal solutions with the same particle concentrations. Since $Yb^{3+}$ ions have no intrinsic absorbency at ca. 800 nm, β-$NaYF_4$:20% Yb,2% Er/$NaYF_4$ and β-$NaYF_4$:30% Yb,0.5% Er/$NaYF_4$ dual doped core/shell UCNPs were employed as reference samples in the measurement, and are denoted as 0% $Nd^{3+}$ doping. The emission spectra and intensity counts of β-core/shell UCNPs are displayed in FIG. 4. Significantly, 0.5% of $Nd^{3+}$ doped UCNPs was found to be the preferred concentration and showed a 28.7-fold enhancement on the green emission peak of the $Er^{3+}$ as compared with the none-$Nd^{3+}$ samples. Such emission gradually decreased as the $Nd^{3+}$ concentration rose to 5%. This indicates that the increase of doped $Nd^{3+}$ will quench the upconverting process, even when the total photon absorbance at 800 nm is raised.

To further confirm the essential roles of the $Nd^{3+}$ and $Yb^{3+}$ in the cascade sensitization upconversion pathway, two other control samples were synthesized: single doped β-$NaYF_4$:2% Er/$NaYF_4$ and non-$Yb^{3+}$ dual doped β-$NaYF_4$:1% Nd, 2% Er/$NaYF_4$ UCNPs. (FIG. 24). Without $Nd^{3+}$ sensitizing, it was found that upconversion intensity of β-$NaYF_4$:2% Er/$NaYF_4$ was as weak as that of β-$NaYF_4$:20% Yb,2% Er/$NaYF_4$ UCNPs under 800 nm excitation. This demonstrates the 800 nm-insensibility of $Yb^{3+}$ ions and the essentiality of $Nd^{3+}$ as the initiator ions in the cascade pathway.

In contrast, without $Yb^{3+}$ bridging, $Nd^{3+}$ only showed deleterious quenching effects to $Er^{3+}$ rather than useful sensitizing, even though their energy levels overlaps. Thus, the three types of dopants are integral parts of the cascade sensitization system. The $Nd^{3+}/Yb^{3+}/Tm^{3+}$ upconversion system was also optimized, with the best enhancement of 23.7-fold from β-$NaYF_4$:1% Nd, 30% Yb, 0.5% Tm/$NaYF_4$ core/shell UCNPs. This is likely due to a lower activator ratio ($Tm^{3+}$ 0.5%) used in the $Nd^{3+}/Yb^{3+}/Tm^{3+}$ system, and the optimal $Nd^{3+}$ ratio increased slightly to 1%. FIGS. 4b and 4d show the optimized β-$NaYF_4$:Nd,Yb,Er(Tm)/$NaYF_4$ core/shell UCNP solutions. Under a 6.0 W/cm² of 800 nm CW laser excitation, the green ($Er^{3+}$, $^2H_{11/2}$, $^4S_{3/2} \rightarrow {}^4I_{15/2}$) and blue ($Tm^{3+}$, $^1G_4 \rightarrow {}^3H_6$) upconverting emissions were clearly observed.

A solution of CdSe/ZnS QDs was placed at the side of the UCNPs solutions as the control. Although QDs are known as excellent multi-photon probes via pulsed laser excitation, there are no detectable emissions from QDs under such a low power 800 nm CW laser. Moreover, it was observed that β-NaYF$_4$ shell coating was able to provide more than a 20-fold enhancement of β-NaYF$_4$:Nd,Yb,Er and a 50-fold enhancement of β-NaYF$_4$:Nd,Yb,Tm core UCNPs (FIG. 25). Thus, such a core/shell structure is important in ensuring the success of multiple-step resonance energy transfer in tri-doped colloid UCNPs. (Su, et al. 2012 *J Am Chem Soc* 134,20849.)

The fitted slope of 800 nm excitation power dependence was 1.79 for the $^4S_{3/2} \rightarrow {}^4I_{15/2}$ transitions of $Er^{3+}$ (2-photon upconversion) and 2.27 for the $^1G_4 \rightarrow {}^3H_6$ transition of $Tm^{3+}$ (3-photon upconversion) (FIG. 26). The rigorous linearity denoted that no excitation saturation occurred. As shown in FIG. 28, the slope values were similar to those of a typical dual-dopant upconversion process under a 980 nm CW laser.

In regard to the secondary sensitizer, the $Yb^{3+}$ ratios were investigated in order to optimize the efficiencies of bridging energy transfer. As shown in FIG. 5, increasing of $Yb^{3+}$ ratio showed no improvement in the $Er^{3+}(Tm^{3+})$ emission yields. The result suggests that 20-30% of $Yb^{3+}$ dopants are sufficient to deliver energy from 1% doped $Nd^{3+}$. On the other hand, it was found that the β-NaYF$_4$:Nd,Yb,Er(Tm)/NaYF$_4$ core/shell UCNPs still maintained their 980 nm excitable upconverting luminescence, which relied only on the sensitizer of $Yb^{3+}$ (FIG. 27). Taking the optimal β-NaYF$_4$:Nd, Yb,Er/NaYF$_4$ UCNPs as examples, the 980 nm motivated emission intensity from 0.5% $Nd^{3+}$ doped UCNPs was ca. 67.8% of the outputs from β-NaYF$_4$:Yb, Er/NaYF$_4$ UCNPs (FIG. 27C), which can be clearly seen in ambient indoor light (FIG. 31).

To test photo-stability, the β-NaYF$_4$:Nd,Yb,Er(Tm)/NaYF$_4$ UCNPs solutions was continuously excited with an 800 nm CW laser for 1 hour. No photo-bleaching was observed (FIG. 29). For purposes of water solubility and future bio-applications, the as-synthesized β-NaYF$_4$:Nd,Yb, Er(Tm)/NaYF$_4$ UCNPs with oleic acid capping were treated by ligand exchange. (Dong, et al. 2011 *J Am Chem Soc* 133, 998.) Modified UCNPs with Poly(acrylic acid) (PAA) coating can disperse well in water to form transparent solutions, with an average hydrodynamic size of 36.7 nm and 41.3 nm for β-NaYF$_4$:0.5% Nd,20% Yb,2% Er/NaYF$_4$ and β-NaYF$_4$: 1% Nd,30% Yb,0.5% Tm/NaYF$_4$ UCNPs, respectively. As shown in FIG. 6, the 800 nm excited upconverting luminescence from their water solutions can be easily seen by the naked eye in room light.

Thus, in one aspect, the invention generally relates to an upconversion luminescence material. The upconversion luminescence material includes: (1) a first Lanthanide, $Ln_{(i)}$, having a mol % from about 0.1% to about 5% (e.g., 0.2%, 0.5%, 1%, 1.5%, 2%, 2.5%, 3%, 3.5%, 4%, 4.5%); (2) a second Lanthanide ion, $Ln_{(j)}$, having a mol % from about 10% to about 80% (e.g., 15%, 20%, 25%, 30%, 35%, 40%, 45%, 50%, 55%, 60%, 65% 70%, 75%); and (3) a third Lanthanide ion, $Ln_{(k)}$, having a mol % from about 0.1 to about 10% (e.g., 0.2%, 0.5%, 1%, 2%, 3%, 4%, 5%, 6%, 7%, 8%, 9%). The upconversion luminescence material is characterized by a constitutional excitation peak substantially away from 980 nm.

Ln here refers to the lanthanide (or lanthanoid), the fifteen metallic chemical elements with atomic numbers 57 through 71, from lanthanum through lutetium.

| Lanthanide | | | | | | | | | | | | | | |
|---|---|---|---|---|---|---|---|---|---|---|---|---|---|---|
| La | Ce | Pr | Nd | Pm | Sm | Eu | Gd | Tb | Dy | Ho | Er | Tm | Yb | Lu |
| 57 | 58 | 59 | 60 | 61 | 62 | 63 | 64 | 65 | 66 | 67 | 68 | 69 | 70 | 71 |

In certain preferred embodiments, the upconversion luminescence material is characterized by a constitutional excitation peak at about 800 nm. In certain preferred embodiments, the upconversion luminescence material is biocompatible.

In certain preferred embodiments, $Ln_{(i)}$ is Nd; $Ln_{(j)}$ is Yb; and $Ln_{(k)}$ is Er, Ho or Tm (preferably Er or Tm).

In certain preferred embodiments, the upconversion luminescence material includes β-NaYF$_4$, CaF$_2$, LiYF$_4$, NaGdF$_4$, NaScF$_4$, α-NaYF$_4$, NaYbF$_4$, NaLaF$_4$, LaF$_3$, GdF$_3$, GdOF, La$_2$O$_3$, Lu$_2$O$_3$, Y$_2$O$_3$, Y$_2$O$_2$S, YbF$_3$, YF$_3$, KYF$_4$, KGdF$_4$, BaYF$_5$, BaGdF$_5$, NaLuF$_4$, KLuF$_4$,BaLuF$_5$ or a mixture of two or more thereof (e.g., in the core and/or shell of nanoparticles).

In certain preferred embodiments, Nd, having a mol % from about 0.2 to about 3% (e.g., from about 0.5% to about 2%); Yb, having a mol % from about 20% to about 70% (e.g., from about 20% to about 50%); and Er or Tm, having a mol % from about 0.2 to about 5% (e.g., from about 0.2% to abut 3%).

In certain preferred embodiments, the upconversion luminescence material is characterized by a nano-structure (e.g., in the form of nanoparticles).

The nanoparticles may have any suitable dimensions, for example, with a dimension the range from about 2 nm to about 150 nm (e.g., from about 2 nm to about 100 nm, from about 3 nm to about 50 nm, from about 5 nm to about 30 nm).

In certain preferred embodiments, the nanoparticles have a core/shell configuration, preferably an epitaxial configuration.

In certain preferred embodiments, the core includes β-NaYF$_4$:Nd,Yb,Er or β-NaYF$_4$:Nd,Yb,Tm; and the shell includes β-NaYF$_4$. In certain embodiments, the core has a dimension from about 1 nm to about 100 nm (e.g., about 2 nm, about 5 nm, about 10 nm, about 20 nm, about 30 nm, about 40 nm, about 50 nm, about 60 nm, about 70 nm, about 80 nm, about 90 nm) and the shell has a dimension from about 1 nm to about 50 nm (e.g., about 2 nm, about 5 nm, about 10 nm, about 20 nm, about 30 nm, about 40 nm). In certain preferred embodiments, the upconversion luminescence material is characterized by an emission spectrum in the visible region, e.g., a peak in the green/yellow region (e.g., at about 540 nm, at about 525 nm) or a peak in the blue region (e.g., at about 474 nm).

In certain preferred embodiments, the nanoparticles have a core/shell/shell configuration comprising an inner shell and an outer shell, preferably in an epitaxial configuration.

In certain preferred embodiments, the core includes β-NaYF$_4$:Yb,Tm; the inner shell includes β-NaYF$_4$:Nd,Yb, Er or β-NaYF$_4$:Nd,Yb,Tm; and the shell include β-NaYF$_4$.

In certain preferred embodiments, the core has a dimension from about 5 nm to about 100 nm (e.g., from about 5 nm to about 80 nm, from about 5 nm to about 60 nm, from about 5 nm to about 50 nm, from about 5 nm to about 30 nm, from about 5 nm to about 20 nm, from about 10 nm to about 100 nm, from about 20 nm to about 100 nm, from about 30 nm to about 100 nm, from about 50 nm to about 100 nm), the inner shell has a dimension from about 1 nm to about 20 nm (e.g., about 1 nm to about 15 nm, about 1 nm to about 10 nm, about 1 nm to about 5 nm, about 2 nm to about 20 nm, about 5 nm to about 20 nm, about 10 nm to about 20 nm), and the outer shell has a dimension from about 1 nm to about 20 nm (e.g., about 1 nm to about 15 nm, about 1 nm to about 10 nm, about 1 nm to about 5 nm, about 2 nm to about 20 nm, about 5 nm to about 20 nm, about 10 nm to about 20 nm). In certain preferred embodiments, the upconversion luminescence material is characterized by an emission spectrum comprising a peak at about 540 nm. In certain preferred embodiments, the upconversion luminescence material is characterized by an emission spectrum in the visible region, e.g., a peak in the green/yellow region (e.g., at about 540 nm, at about 525 nm) or a peak in the blue region (e.g., at about 474 nm).

In another aspect, the invention generally relates to a biocompatible upconversion luminescence nanoparticle, which include: a tri-doped core of β-NaYF$_4$: Ln$_{(i)}$,Ln$_{(j)}$, Ln$_{(k)}$; and an epitaxial shell of β-NaYF$_4$, wherein Ln$_a$) is Nd; Ln$_{(j)}$ is Yb; and Ln$_{(k)}$ is Er, Ho or Tm.

The term "biocompatible", as used herein, refers to a material that is compatible with living cells, tissues, organs or systems, and poses minimal or no risk of injury, toxicity, or rejection by the immune system. A biocompatible material may be a synthetic or natural material used to replace part of a living system or to function in intimate contact with living tissue. Biocompatible materials typically interface with biological systems to evaluate, treat, augment or replace any tissue, organ or function of the body.

In certain preferred embodiments, the upconversion luminescence is characterized by a constitutional excitation peak at about 800 nm.

In certain embodiments, Nd accounts for a mol % from about 0.1% to about 5% of the core (e.g., 0.2%, 0.5%, 1%, 1.5%, 2%, 2.5%, 3%, 3.5%, 4%, 4.5%); Yb accounts for a mol % from about 10% to about 80% of the core (e.g., 15%, 20%, 25%, 30%, 35%, 40%, 45%, 50%, 55%, 60%, 65% 70%, 75%); and Er or Tm accounts for a mol % from about 0.1 to about 10% of the core (e.g., 0.2%, 0.5%, 1%, 2%, 3%, 4%, 5%, 6%, 7%, 8%, 9%).

In certain preferred embodiments, Nd accounts for a mol % from about 0.2 to about 3% of the core; Yb accounts for a mol % from about 20% to about 70% of the core; and Er or Tm accounts for a mol % from about 0.2 to about 5% of the core.

In certain preferred embodiments, the biocompatible upconversion luminescence nanoparticle is characterized by an emission spectrum in the visible region, e.g., a peak at about 540 nm, at about 525 nm, and/or at about 474 nm).

The biocompatible upconversion luminescence nanoparticle may include a chemically modified and/or functionalized surface, such as by poly(acrylic acid), citric acid, and molecules with —COOH or —NH$_2$ groups, for example. A variety of groups and chemistries are available for such functionalization. (Zhou, et al. 2012 Chem. Soc. Rev. 41, 1323-1349.)

In yet another aspect, the invention generally relates to a biocompatible upconversion luminescence nanoparticle, which includes: a core of β-NaYF$_4$: Ln$_{(j)}$, Ln$_{(k)}$; an epitaxial inner shell of β-NaYF$_4$: Ln$_{(i)}$,Ln$_{(j)}$,Ln$_{(k)}$; and an epitaxial outer shell of β-NaYF$_4$. Ln$_{(i)}$ is Nd; Ln$_{(j)}$ is Yb; and Ln$_{(k)}$ is Er or Tm.

In certain preferred embodiments, the upconversion luminescence is characterized by a constitutional excitation peak at about 800 nm.

In certain embodiments, Nd accounts for a mol % from about 0.1% to about 5% of the inner shell (e.g., 0.2%, 0.5%, 1%, 1.5%, 2%, 2.5%, 3%, 3.5%, 4%, 4.5%); Yb accounts for a mol % from about 10% to about 80% of the inner shell (e.g., 15%, 20%, 25%, 30%, 35%, 40%, 45%, 50%, 55%, 60%, 65% 70%, 75%); and Er or Tm accounts for a mol % from about 0.1 to about 10% of the inner shell (e.g., 0.2%, 0.5%, 1%, 2%, 3%, 4%, 5%, 6%, 7%, 8%, 9%).

In certain preferred embodiments, the core has a dimension from about 5 nm to about 100 nm (e.g., from about 5 nm to about 80 nm, from about 5 nm to about 60 nm, from about 5 nm to about 50 nm, from about 5 nm to about 30 nm, from about 5 nm to about 20 nm, from about 10 nm to about 100 nm, from about 20 nm to about 100 nm, from about 30 nm to about 100 nm, from about 50 nm to about 100 nm), the inner shell has a dimension from about 1 nm to about 20 nm (e.g., about 1 nm to about 15 nm, about 1 nm to about 10 nm, about 1 nm to about 5 nm, about 2 nm to about 20 nm, about 5 nm to about 20 nm, about 10 nm to about 20 nm), and the outer shell has a dimension from about 1 nm to about 20 nm (e.g., about 1 nm to about 15 nm, about 1 nm to about 10 nm, about 1 nm to about 5 nm, about 2 nm to about 20 nm, about 5 nm to about 20 nm, about 10 nm to about 20 nm). In certain preferred embodiments, the upconversion luminescence material is characterized by an emission spectrum comprising a peak at about 540 nm. In certain preferred embodiments, the upconversion luminescence material is characterized by an emission spectrum in the visible region, e.g., a peak in the green/yellow region (e.g., at about 540 nm, at about 525 nm) or a peak in the blue region (e.g., at about 474 nm).

In yet another aspect, the invention generally relates to a sensing probe for detecting a target molecule in a sample. The sensing probe includes an upconversion luminescence material and/or a biocompatible upconversion luminescence nanoparticle disclosed herein.

In yet another aspect, the invention generally relates to a method for detecting a target molecule in a sample. The method includes: providing a sensing probe comprising an upconversion luminescence nanoparticle having a constitutional excitation peak at about 800 nm, wherein the sensing probe is capable of association with the target molecule; contacting the sensing probe with a sample to be tested for the presence of the target molecule under a condition such that if the target molecule is present the sensing probe becomes associated with the target molecule; exciting the sensing probe with an excitation at about 800 nm; and detecting an emission at a shorter wavelength than 800 nm to determining the presence of the target molecule.

The target molecule may be any suitable molecules. Exemplary target molecules include proteins (including peptides, antibodies, enzymes) and nucleic acids (including oligonucleotides). The biocompatible upconversion luminescence nanoparticle can be chemically coupled to or otherwise associated with various target molecules.

In yet another aspect, the invention generally relates to an imaging system comprising an upconversion luminescence material and/or an upconversion luminescence nanoparticle of the invention.

In yet another aspect, the invention generally relates to a photonics system comprising an upconversion luminescence material and/or an upconversion luminescence nanoparticle of the invention. As used herein, the term "photonics" refers to the generation, emission, transmission, modulation, signal processing, switching, amplification, and detection/sensing of light.

The invention disclosed herein allowed for the first time the constitutional excitation wavelength of colloidal dispersible UCNPs to be engineered. In particular, Nd$^{3+}$/Yb$^{3+}$/Er$^{3+}$ (Tm$^{3+}$) tri-doped core/shell β-NaYF$_4$ colloidal UCNPs with a constitutional biocompatible 800 nm excitable property were successfully developed. The cascade sensitized tri-dopants upconversion nanoparticle system was well optimized for ideal intra-$Ln^{3+}$ energy transfer. The optimized β-$NaYF_4$:Nd,Yb,Er(Tm)/$NaYF_4$ UCNPs are characterized by a monodispersed size of about 29 nm, and a more than 20-fold enhancement of emission yield under 800 nm CW laser excitation with no photo-bleaching. Significantly, upon surface modification, such upconversion luminescence in aqueous phase is still found to be easily visible to the naked eye in ambient light, showing comparable efficiency with traditional 980 nm CW laser excitation. The tri-dopants core/shell UCNPs of the invention thus open the door to engineering the excitation wavelengths of upconversion nanoparticles and provide a powerful tool for a wide variety of applications in the fields of biophotoics and photonics.

EXAMPLES

Synthesis of β-$naYF_4$:Ln Core UCNPs

The β-$NaYF_4$:Ln Core UCNPs were prepared by a two-step thermolysis method [23]. In the first step, $CF_3COONa$ (0.5 mmol) and proper $Ln(CF_3COO)_3$ (0.5 mmol in total) precursors were mixed with oleic acid (5 mmol), oleyl amine (5 mmol) and 1-octadecene (10 mmol) in a two-neck reaction flask. The slurry mixture was heated to 110° C. to form a transparent solution followed by 10 minutes of degassing. Then the flask was heated to 300° C. with a rate of 15° C./min under dry argon flow, and it maintained at 300° C. for 30 minutes. The α-$NaYF_4$:Ln intermediate UCNPs were gathered from the cooled reaction solution by centrifugal washing with excessive ethanol. In the second step, the α-$NaYF_4$:Ln intermediate UCNPs were re-dispersed into oleic acid (10 mmol) and 1-octadecene (10 mmol) together with $CF_3COONa$ (0.5 mmol) in a new two-neck flask. After degassing at 110° C. for 10 minutes, this flask was heated to 325° C. with a rate of 15° C./min under dry argon flow, and remained at 325° C. for 30 minutes. Then, β-$NaYF_4$:Ln UCNPs were centrifugally separated from the cooled reaction media and preserved in hexane (10 mL) as stock solution.

Synthesis of β-$naYF_4$:Ln/$NaYF_4$ Core/Shell UCNPs

The as-synthesized β-$NaYF_4$:Ln UCNPs served as core nanoparticles for epitaxial growth of the undoped β-$NaYF_4$ shell. Typically, 5.0 mL of the β-$NaYF_4$:Ln UCNPs stock solution (ca. 0.25 mmol of total $Ln^{3+}$) was transferred into a two-neck flask and the hexane was evaporated by heating. Then $CF_3COONa$ (0.5 mmol) and $Y(CF_3COO)_3$ (0.5 mmol) were introduced as β-$NaYF_4$ shell precursors together with solvents of oleic acid (10 mmol) and 1-octadecene (10 mmol). After 10 minutes of degassing at 110° C., the flask was heated to 325° C. at a rate of 15° C./min under argon protection, and was maintained at 325° C. for 30 minutes. The products can be precipitated by adding ethanol to the cooled reaction flask. After centrifugal washing with hexane/ethanol, the core/shell UCNPs were re-dispersed in hexane (10 mL).

Surface Modification or Water-soluble Core/Shell UCNPs

The hydrophobic oleic acid coated β-$NaYF_4$:Ln/$NaYF_4$ UCNPs were transferred into water using a modified $NOBF_4$ treating route. ( )Dong, et al. 2011 *J Am Chem Soc* 133, 998. In the first step, nitrosonium tetrafluoroborate ($NOBF_4$, 0.20 g) was dissolved in dimethylformamide (DMF, 5 mL), and the β-$NaYF_4$:Ln/$NaYF_4$ UCNPs in hexane stock solution (1 mL) were added, followed by 2 h of stirring in a sealed pot at room temperature. Then the $BF_4^-$ capped UCNPs were precipitated by adding an isopropanol/hexane mixture at 1:1 volume ratio, and purified by 2 cycles of centrifugal wash with DMF. In the second step, all of the UCNPs precipitate were dispersed in Poly(acrylic acid) (PAA, $M_w$ 1800) solution (PAA 100 mg, DMF 10 mL) to replace surface $BF_4^-$ with PAA. After overnight incubation, the PAA coated UCNPs were purified by centrifugal wash with DI water, and dispersed in 5 mL of DI water.

Synthesis of Core/Shell/Shell 800 nm Excitable UCNPs

In this UCNP architect, for example, β-$NaYF_4$:(20-99.5%)Yb, 0.5% Tm/β-$NaYF_4$(20-80%)Nd, 10% Yb/β-$NaYF_4$ core/shell/shell UCNPs, $Nd^{3+}$ concentration can be elevated, thus providing improved upconversion emission outcomes.

Typical synthetic protocols are described below. Exemplary TEM images of core-shell and core-shell-shell are shown in FIG. 32. The emission spectra of core-shell and core-shell-shell UCNPs under excitation of an 800 nm CW diode laser are shown in FIG. 33.

1. Synthesis Protocol for β-$naYF_4$:99.5% Yb, 0.5% Tm Core UCNPs

The β-$NaYF_4$:99.5% Yb, 0.5% Tm Core UCNPs were prepared using a modified two-step thermolysis method. (Mai, et al. 2006 *J. Am. Chem. Soc.* 128, 6426.) In the first step, the $CF_3COONa$ (1 mmol) and required $Ln(CF_3COO)_3$ (0.5 mmol in total, 99.5% Yb, 0.5% Tm) precursors were mixed with oleic acid (5 mmol), oleyl amine (5 mmol) and 1-octadecene (10 mmol) in a two-neck reaction flask. The slurry mixture was heated to 110° C. in order to form a transparent solution. This was followed by 10 minutes of degassing to remove the oxygen and water. The flask was then heated to 300° C. at a rate of 15° C./min under dry argon flow, and remained at 300° C. for 30 minutes. The α-$NaLnF_4$ intermediate UCNPs were acquired by cooling down the reaction solution to room temperature, followed by centrifugation with excessive ethanol. In the second step, the α-$NaYF_4$: 99.5% Yb, 0.5% Tm UCNPs were re-dispersed in oleic acid (10 mmol) and 1-octadecene (10 mmol) along with $CF_3COONa$ (0.5 mmol) in a two-neck flask. After degassing at 110° C. for 10 minutes, the flask was heated to 325° C. at a rate of 15° C./min under dry argon flow, and remained at 325° C. for 30 minutes. The β-$NaYF_4$:Yb,Tm UCNPs were then centrifugally separated from the cooled reaction media and suspended in 10 mL of hexane as the stock solution for further use.

2. Synthesis of β-$naYF_4$:99.5% Yb, 0.5% Tm@$NaYF_4$:50% Nd, 10% Yb (Core/Shell) UCNPs In this thermolysis reaction, as-synthesized β-$NaYF_4$: 99.5% Yb, 0.5% Tm UCNPs served as crystallization seeds for the epitaxial growth of undoped β-$NaYF_4$ shell. Typically, a stock solution of β-$NaYF_4$:Yb,Tm UCNPs (5 mL, ca. 0.26 μmol/L core UCNPs) was transferred into a two-neck flask and hexane was sequentially removed by heating. Then $CF_3COONa$ (0.5 mmol) and $Ln(CF_3COO)_3$ (0.5 mmol) were introduced as UCNP shell precursors with oleic acid (10 mmol) and 1-octadecene (10 mmol). After 10 minutes of degassing at 110° C., the flask was heated to 325° C. at a rate of 15° C./min under dry argon flow and was kept at 325° C. for 30 minutes. The products were precipitated by adding ethanol to the cooled reaction flask. After centrifugal washing with hexane/ethanol, the core/shell UCNPs were re-dispersed in 10 mL of hexane for spectra characterization.

3. Synthesis of β-$naYF_4$:99.5% Yb, 0.5% Tm@$NaYF_4$:50% Nd, 10% Yb@ $NaYF_4$ (Core/Shell/Shell) UCNPs The synthetic procedure of β-$NaYF_4$:99.5% Yb, 0.5% Tm@$NaYF_4$:50% Nd, 10% Yb@$NaYF_4$ was the same as that used to synthesize β-$NaYF_4$:99.5% Yb, 0.5% Tm@$NaYF_4$:50% Nd, 10% Yb UCNPs nanocrystals, except that 0.5 mmol CF3COONa, 0.5 mmol Y(CF3COO)$_3$ and the 10 ml β-NaYF$_4$:99.5% Yb, 0.5% Tm@NaYF$_4$:50% Nd nanocrystals prepared were added to a mixture of OA (10 mmol) and ODE (10 mmol) in a three-necked flask. The final core-shell-shell UCNPs were re-dispersed in 10 mL of hexane for spectra characterization.

Materials

Y$_2$O$_3$ (99.9%), Nd$_2$O$_3$ (99.9%), Yb$_2$O$_3$ (99.9%), Er$_2$O$_3$ (99.9%), Tm$_2$O$_3$ (99.9%), CF$_3$COONa (99.9%), CF$_3$COOH, 1-octadecene (90%), oleic acid (90%), oleyl amine (90%), were all purchased from Sigma-Aldrich and used without further purification. The lanthanide (Ln) trifluoroacetates, Ln(CF$_3$COO)$_3$, were prepared as literature described. (Roberts 1961 *J Am Chem Soc* 83, 1087) CdSe/ZnS quantum dots (QE=45%, $\lambda_{em}$ 530 nm) were synthesized as described previously. (Talapin, et al. 2001 *Nano Lett* 1, 207.)

The Volume Ratio of Core and Shell Components

The average diameters of sphere-like core and core/shell UCNPs are 20 nm (d) and 29 nm (D) respectively, so the approximative volume ratio of inner β-NaYF$_4$:Nd,Yb,Er (Tm) core and outer β-NaYF$_4$ shell can be expressed by the following formula:

$$V_{core}/V_{shell} = \pi d^3/6 \div (\pi D^3/6 - \pi d^3/6) = d^3/(D^3 - d^3) = 1:2.05$$

UCNPs Concentration

In this research, all core and core/shell UCNP samples had monodisperse size distributions. The epitaxial growth of undoped β-NaYF$_4$ shell was supposed to perform relatively fixed output yields for all core UCNPs, together with the uniform diameter of core (ca. 20 nm) and core/shell (ca. 29 nm) UCNPs, and the consistent value between the precursors input ratio and core/shell volume ratio. Thus, it can be concluded that all types of β-core/shell UCNP samples have the similar synthesis yields and their final stock solutions had the similar particle concentrations.

The approximate volume of a β-NaYF$_4$ unit cell (Na$_{1.5}$Y$_{1.5}$F$_6$, a=0.596 nm, c=0.353 nm) single core/shell particle (D=29 nm) can be calculated with the following formulas:

$$V_0 = 3^{1/2} \times a^2 \times c \div 2 = 0.1086 \text{ nm}^3$$

$$V_{UCNP} = \pi D^3/6 = 12763 \text{ nm}^3$$

Therefore, the approximate amount of Ln$^{3+}$ ions in a single β-core/shell nanosphere can be calculated with the following formulas:

$$Ln^{3+} = 1.5 \times V_{UCNP}/V_0 = 1.18 \times 10^5$$

If we assume the synthesis yield is 90%, the approximate particle concentrations in β-core/shell UCNPs stock solutions can be calculated with the following formulas:

$$c = (0.25 + 0.5) \text{ mmol} \times 90\%/118000 \div 10 \text{ mL} = 0.57 \text{ μmol/L}$$

Surface Ln$^{3+}$ Proportion on β-NaLnF$_4$ UCNPs

The amount of Ln$^{3+}$ ions in the outermost layer of unit cells of UCNPs is estimated using the following approach. A hexagonal phased (β) NaYF$_4$ unit cell prism has the following parameters: a=0.596 nm, c=0.353 nm. The length of its longer body diagonal can be calculated with the following formula:

$$d = (c^2 + 3 \times a^2)^{1/2} = 1.091 \text{ nm}.$$

Due to the global curvature of the UCNPs, it is complicated to count all of the unit cells that are exposed on the UCNP surface. A simpler way is to define the thickness of a continual layer of these outmost unit cells and then calculate the sum volume. Considering the disorder and defects in the lattice packing on the UCNP surface, we defined the length of d as the reasonable thickness of the outmost unit cells layer. Therefore, the proportion of surface Ln$^{3+}$ can be calculated by the following equation:

$$n_{surface}/n_{tatol} = V_{surface}/V_{tatol} = [r^3 - (r-d)^3]/r^3$$

where r is the radius of the spherical UCNPs. For a 20 nm β-NaLnF$_4$ UCNP, we can estimate that its surface Ln$^{3+}$ account is ca. 29% in total Ln$^{3+}$ quantity. Since all dopants are homogeneously dispersed in β-NaLnF$_4$ nanosphere, the surface expose probability is also 29% for each kind of Ln$^{3+}$ dopant.

Spectra Characterization

All upconversion luminescence spectra were measured by a SPEX Fluoromax-3 spectrofluorimeter (Horiba) (spectral resolution of 0.5 nm, emission slit of 1 nm, and integral period of 0.2 s) that was equipped with a continuous wave (CW) laser. The NIR laser was introduced into the spectrofluorimeter chamber using an optical fiber and focused by a convex lens. The approximate diameter of the focused laser beam is 1.8 mm, fitted by a pinhole (beam cross-section area 0.025 cm$^2$). The total laser power at the cuvette site was measured by a Newport co. optical power meter. For the sake of quantifying emission intensities, all UCNPs in hexane solution had the same particle concentrations (0.57 μmol/L). For power dependence study, the laser power was modulated by current control in the measurement.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. An upconversion luminescence material characterized by a nano-structure in the form of nanoparticles having a core/shell/shell configuration comprising an inner shell and an outer shell in an epitaxial configuration, wherein comprising
the core comprises β-NaYF4:Yb,Tm;
the inner shell comprises β-NaYF$_4$:Nd,Yb,Er or β-NaYF$_4$:Nd,Yb,Tm; and
the shell comprises β-NaYF$_4$,
wherein
Nd is present at a mol % from about 0.1% to about 10%;
Yb is present at a mol % from about 10% to about 80%; and
Er or Tm is present at a mol % from about 0.1 to about 10%; and
the upconversion luminescence material is characterized by a constitutional excitation peak away from 980 nm.

2. The upconversion luminescence material of claim 1, wherein the upconversion luminescence material is characterized by a constitutional excitation peak at about 800 nm.

3. The upconversion luminescence material of claim 1, further comprising $CaF_2$, $LiYF_4$, $NaGdF_4$, $NaScF_4$, α-NaYF4, $NaYbF_4$, $NaLaF_4$, $LaF_3$, $GdF_3$, GdOF, $La_2O_3$, $Lu_2O_3$, $Y_2O_3$, $Y_2O_2S$, or a mixture of two or more thereof.

4. The upconversion luminescence material of claim 3, comprising:
Nd, having a mol % from about 0.2 to about 5%;
Yb, having a mol % from about 20% to about 70%; and
Er or Tm, having a mol % from about 0.2 to about 5%.

5. The upconversion luminescence material of claim 1, wherein the upconversion luminescence material is characterized by an emission spectrum comprising a peak at about 540 nm, at about 525 nm or at about 474 nm.

6. A sensing probe for detecting a target molecule in a sample, comprising an upconversion luminescence material of claim 1, wherein the target molecule is selected from a protein, an antibody, an enzyme or a nucleic acid molecule.

* * * * *